(12) United States Patent
Clynne et al.

(10) Patent No.: US 11,666,674 B2
(45) Date of Patent: Jun. 6, 2023

(54) LIGHT DISINFECTION SYSTEM AND METHOD

(71) Applicant: CURRENT LIGHTING SOLUTIONS, LLC, East Cleveland, OH (US)

(72) Inventors: Thomas Clynne, East Cleveland, OH (US); Gary R. Allen, Euclid, OH (US); Kevin J. Benner, Solon, OH (US); Kevin J. Vick, Cleveland Heights, OH (US); Erik L. Kvam, Niskayuna, NY (US)

(73) Assignee: Current Lighting Solutions, LLC, East Cleveland, OH (US)

( * ) Notice: Subject to any disclaimer, the term of this patent is extended or adjusted under 35 U.S.C. 154(b) by 0 days.

(21) Appl. No.: 17/581,120

(22) Filed: Jan. 21, 2022

(65) Prior Publication Data

US 2022/0143241 A1 May 12, 2022

Related U.S. Application Data

(63) Continuation of application No. 17/026,859, filed on Sep. 21, 2020, now Pat. No. 11,541,136, which is a
(Continued)

(51) Int. Cl.
*A61L 2/10* (2006.01)
*A61L 2/00* (2006.01)
(Continued)

(52) U.S. Cl.
CPC .............. *A61L 2/10* (2013.01); *A61L 2/0047* (2013.01); *A61L 2/084* (2013.01); *A61L 2/24* (2013.01);
(Continued)

(58) Field of Classification Search
CPC .......... A61L 2/10; A61L 2/0047; A61L 2/084; A61L 2/24; A61L 9/20; A61L 2202/11;
(Continued)

(56) References Cited

U.S. PATENT DOCUMENTS 4,974,922 A   12/1990   Mori
5,874,701 A * 2/1999   Watanabe .............. B01D 53/86
                                                 204/158.21
(Continued)

OTHER PUBLICATIONS

International Search Report dated Nov. 14, 2016 corresponding to International Application No. PCT/US2016/021899.
(Continued)

*Primary Examiner* — Kiet T Nguyen
(74) *Attorney, Agent, or Firm* — Lippes Mathias LLP

(57) ABSTRACT

A lighting system includes a light source configured to generate light to inactivate one or more pathogens. The light includes an inactivating portion. In one embodiment, a method for inactivating one or more pathogens and optionally concurrently illuminating a room having one or more human occupants while the pathogens are inactivated is also provided. The method includes generating light from a light source to inactivate the one or more pathogens. The light is generated with an inactivating portion of the light.

20 Claims, 14 Drawing Sheets

Related U.S. Application Data continuation-in-part of application No. 15/990,296, filed on May 25, 2018, now Pat. No. 10,960,090, which is a continuation-in-part of application No. 15/429,773, filed on Feb. 10, 2017, now Pat. No. 9,981,052, which is a continuation of application No. 15/065,894, filed on Mar. 10, 2016, now Pat. No. 9,937,274.

(60) Provisional application No. 62/134,954, filed on Mar. 18, 2015.

(51) Int. Cl.
*A61L 2/08* (2006.01)
*A61L 2/24* (2006.01)
*A61L 9/20* (2006.01)

(52) U.S. Cl.
CPC ............. *A61L 9/20* (2013.01); *A61L 2202/11* (2013.01); *A61L 2202/20* (2013.01); *A61L 2202/25* (2013.01)

(58) Field of Classification Search
CPC ............. A61L 2202/25; A61L 2202/14; A61L 2202/20
USPC .................................................. 250/455.11
See application file for complete search history.

(56) References Cited

U.S. PATENT DOCUMENTS

| | | |
|---|---|---|
| 6,139,803 A | 10/2000 | Watanabe et al. |
| 8,398,264 B2 | 3/2013 | Anderson et al. |
| 9,039,966 B2 | 5/2015 | Anderson et al. |
| 2008/0234670 A1 | 9/2008 | Rogers |
| 2008/0265179 A1 | 10/2008 | Havens et al. |
| 2009/0192437 A1 | 7/2009 | Soltz et al. |
| 2010/0246169 A1 | 9/2010 | Anderson et al. |
| 2011/0251657 A1 | 10/2011 | Miyake et al. |
| 2015/0367008 A1 | 12/2015 | Romo et al. |
| 2016/0106873 A1 | 4/2016 | Dobrinsky et al. |
| 2016/0128526 A1 | 5/2016 | Dobrinsky et al. |
| 2017/0080246 A1 | 3/2017 | Knight |
| 2022/0001069 A1* | 1/2022 | Allen ........................ A61L 2/24 |

OTHER PUBLICATIONS

Written Opinion of the International Searching Authority dated Nov. 14, 2016 corresponding to International Application No. PCT/US2016/021899.

International Preliminary Report on Patentability dated Sep. 19, 2017 corresponding to International Application No. PCT/US2016/021899.

* cited by examiner

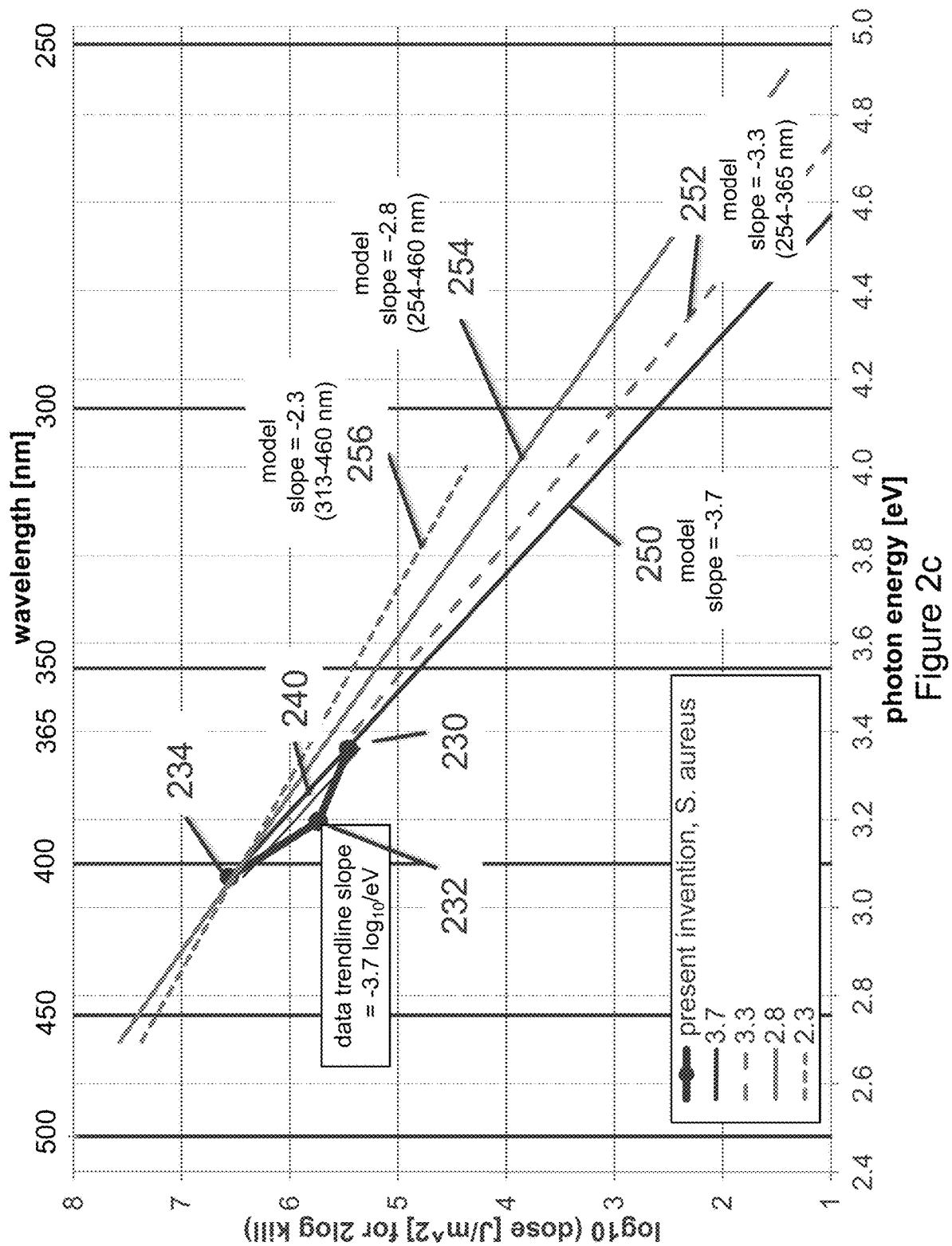

LIGHT DISINFECTION SYSTEM AND METHOD

CROSS-REFERENCE TO RELATED APPLICATIONS

This application is a continuation of U.S. Ser. No. 17/026,859 filed Sep. 21, 2020 which is a continuation-in-part of U.S. application Ser. No. 15/990,296, filed 25 May 2018 (now U.S. Pat. No. 10,960,090) which is a continuation-in-part of U.S. application Ser. No. 15/429,773 filed on Feb. 10, 2017 (now U.S. Pat. No. 9,981,052) which is a continuation of U.S. application Ser. No. 15/065,894 filed on Mar. 10, 2016 (now U.S. Pat. No. 9,937,274) which claims priority to U.S. Provisional Application No. 62/134,954 filed Mar. 18, 2015. The entire disclosures of all the aforementioned applications and patents are hereby incorporated herein by reference.

FIELD

Embodiments of the subject matter disclosed herein relate to lighting systems that disinfect surfaces and materials of pathogens (i.e., inactivate the pathogens).

BACKGROUND

Light has been used to disinfect pathogens on surfaces, in air, or in water (i.e. to inactivate pathogens in fluids, or on solid surfaces). Herein the term "pathogen" refers to any microscopic organism capable of causing disease or infection in a human. These include bacteria, viruses, spores, and fungi. Herein the term "inactivate" refers to rendering a pathogen inactive, or unable to infect a human. This may include killing the pathogen, rendering it unable or less able to replicate, or rendering it unable to infect a human. Some known systems use ultraviolet (UV) light to inactivate pathogens. Herein, we adopt the standard definitions, as follows: ultraviolet light refers to light having wavelengths in the range 100 nanometers (nm) to 400 nm; the four sub-ranges within the UV range include the Vacuum UV from 100 to 200 nm; UVC from 200 to 280 nm; UVB from 280 to 315 nm; and UVA from 315 to 400 nm. Although the visible colors are not rigorously defined in the lighting industry, herein we adopt commonly used definitions for violet and blue as comprising about 400 to about 450 nm, and about 450 to about 490 nm, respectively. Some known systems use UV light in the range of 200 to 300, including the UVC range and some of the UVB range, to inactivate pathogens by damaging their DNA or RNA and rendering them incapable of reproduction, thus incapable of causing disease in humans. This range of 200 to 300 nm is referred to in the literature, and herein, as the germicidal range. Light sources such as low-pressure and medium-pressure mercury lamps, and pulsed xenon lamps are known to inactivate pathogens by irradiation of fluids (e.g. water or air or other fluids) and surfaces with wavelengths in the germicidal range.

A description, with references, of disinfection lighting using the germicidal range of light is found in a recent publication "Light based anti-infectives: ultraviolet C irradiation, photodynamic therapy, blue light, and beyond", Yin et al., Curr Opin Pharmacol, 2013 October. Light of these wavelengths can have high inactivation rates for many types of pathogens on surfaces, in air, or in water. But exposure to light of these germicidal wavelengths can be hazardous to human beings. As a result, these systems may only be used safely in locations where human beings are not present or are prevented from accessing.

Other systems may use violet, blue, or longer wavelengths of visible light to inactivate most common pathogens, but the inactivation rates of the visible wavelengths have been found to be three to five orders of magnitude lower than for the germicidal range of wavelengths of light.

U.S. Pat. No. 8,398,264 describes a lighting device that emits visible light at a wavelength and irradiance sufficient to inactivate one or more pathogenic bacterial species. U.S. Pat. No. 9,039,966 describes a method wherein the visible light for inactivating the MRSA pathogen includes wavelengths in the range of 400-420 nm, i.e., violet light. But these visible light, especially violet light, systems have several problems: disinfecting pathogens with visible light requires a very large flux density of light (e.g. about 0.5 to about 5 $W/m^2$) incident for several hours on the surface to be disinfected; if violet light is used for disinfection, the amount of electrical power required to operate the visible LEDs at sufficient dose to inactivate about 90-99% of a population of common pathogens is so high that the overall efficacy of the lighting system is significantly reduced, by as much as about 10% to about 50% or more; if violet or blue light is used for disinfection, the flux of violet light in the space occupied by humans is so large that some occupants suffer eyestrain, headaches, nausea, dizziness or discomfort; if violet or blue light is used for disinfection, the flux of violet or blue light is so large that it greatly distorts the color point of the white light with which it might be mixed, and is so large that the flux may not be substantially increased for the benefit of more effective disinfection without exceeding the permissible limit of the blue light photobiological hazard standard, rendering the light source unsafe for humans. The limited magnitude of disinfection is a problematic limitation of violet light. The 90-99% inactivation is typically achieved only under certain favorable conditions for disinfection of an architectural space, including the following factors: vegetative bacteria, possibly excluding spores and viruses; in direct line-of-sight of, and in sufficient proximity to the disinfecting light source; and absence of biofilm; with significantly lower inactivation rates for spores and viruses. In most non-ideal circumstances, the inactivation rate may be considerably less than about 90-99%, and may therefore be ineffective, e.g. under circumstances of lower flux levels due to shadowing or distance from the disinfecting light source; biofilm or high bio-burden; spores, or viruses. As a result, these systems are expensive, energy-inefficient, visually obtrusive, physiologically disturbing to some individuals, marginally safe for human exposure, and limited in the magnitude of disinfection by the compromises in system design required to overcome these problems. The term "common pathogen" herein refers to a pathogen that is commonly responsible for human disease, especially in the context of the most commonly encountered nosocomial infections, so-called hospital acquired infections (HAI), including the well-known pathogens *Staphylococcus aureus* (*S. aureus*); Methicillin-resistant *Staphylococcus aureus* (MRSA); *Clostridium difficile* (*C. diff.*); *Escherichia coli* (*E. coli.*); and several other gram-positive, gram-negative, spore, viral, and fungal pathogens.

Other systems may use visible light having wavelengths centered on 405 nm light to provide inactivation of about 90-99% of a pathogen population for many common pathogens, but only if the light source generates the disinfecting light for extended periods of time (i.e., five to ten hours or more of exposure time), and if the disinfecting light is generated at significantly large radiant power densities. The dose of light for inactivation of about 90% of a population of common pathogens using 405 nm light is typically about 10-20 J/cm$^2$, per the reference Maclean et al., High-Intensity Narrow-Spectrum Light Inactivation And Wavelength Sensitivity Of *Staphylococcus Aureus*, FEMS Microbiol Lett 285 (2008) 227-232. This corresponds to an irradiance of 3.5-7 W/m$^2$ of 405 nm light, for an exposure time of 8 hours. Given the typical efficiency of 405 nm LEDs today of about 20-30% (efficiency of converting electrical power to radiated optical power) the disinfection lighting requires an electrical power density of about 12-35 W$_{el}$/m$^2$. The electrical power density used for general white-light illumination at a level of 500 lux from a light source having a typical efficacy of 100 LPW is about 5 W$_{el}$/m$^2$. If the disinfection lighting, providing about 90-99% disinfection on a target surface is added to, and mixed with, the white lighting having a flux density of about 500 lux on the target surface, then the electrical power density of the combined lighting system will be about 17-40 W$_{el}$/m$^2$ Since the electrical power density required for disinfection using 405 nm light is much greater than that required for white-light illumination, the overall system efficacy of the illuminating and disinfecting lighting system may be reduced by as much as about 70-90%, from typically 100 LPW to about 10-30 LPW.

The American Society of Heating, Refrigerating, and Air-Conditioning Engineers (ASHRAE) Energy Standard 90.1-2013 provides an upper limit for the Lighting Power Density (LPD) in the range of about 0.5 to about 2.0 W$_{el}$/ft$^2$, or about 5 to about 20 W$_{el}$/m$^2$ in typical indoor lighting applications. Specifically, for a hospital, the upper limit LPD allowed is 1.05 W$_{el}$/ft$^2$, or 11.3 W$_{el}$/m$^2$, calculated by the Building Area Method. For the typical values given above for a disinfection lighting system using 405 nm light, the LPD of about 17-40 W$_{el}$/m$^2$ exceeds the ASHRAE limit of 11.3 W$_{el}$/m$^2$. The ASHRAE limit would also constrain the flux of the disinfection portion of the lighting (the 405 nm radiation) to no more than about 6 W$_{el}$/m$^2$ which is insufficient to inactivate 90-99% of pathogens over a period of 8 hours using 405 nm light. The ASHRAE limits may adversely affect the ability of customers to use 405 nm disinfection lighting in some regulated applications.

United States Patent Application No. US2011/0251657 A1 describes a lighting device that emits visible light and UVA light in the range 320-380 nm at an irradiance that is in the range of 3 to 15% of the irradiance of the visible light, wherein the visible light provides 700 lux at the work surface, sufficient to activate the human serotonin nervous system with the advantage of decreasing aggressiveness in humans. When the radiant energy of the near ultraviolet radiation with a wavelength of 320 nm or longer, but shorter than 380 nm, is less than 3% of the radiant energy of the visible light, advantageous effects on the serotonin nervous system would not be obtained. Since the visible light used provided 700 lux, and since 3% or more of the radiant energy in the UVA is required to activate the serotonin nervous system, then it may be expected that about 4% or more of the radiant energy should be emitted in the UVA if the visible light component is only 500 lux, instead of 700 lux in order to activate the human serotonin nervous system.

BRIEF DESCRIPTION

In one embodiment, a lighting system includes a light source configured to generate light to inactivate one or more pathogens. The light includes an inactivating portion having wavelengths in a range of 280 to 380 nanometers.

In one embodiment, a method for inactivating one or more pathogens and optionally concurrently illuminating a room having one or more human occupants while the pathogens are inactivated is provided. The method includes generating light from a light source to inactivate the one or more pathogens. The light is generated with an inactivating portion of the light including wavelengths in a range of about 280 to about 380 nanometers.

In one embodiment, a lighting system includes a light source configured to generate light to inactivate one or more pathogens. The light source is configured to generate an inactivating portion of the light including wavelengths in a range of 280 to 380 nanometers, including no more than 0.001 watts of actinic ultraviolet light per square meter of floor area, including no more than 10 watts per square meter of floor area of ultraviolet A light, and including no more than 100 watts of blue light per steradian per square meter of floor area.

BRIEF DESCRIPTION OF THE DRAWINGS

The subject matter described herein will be better understood from reading the following description of non-limiting embodiments, with reference to the attached drawings, wherein below:

FIG. 2*c* illustrates the dataset with a linear trend line from FIG. 2*b* with several lines representing the dose vs. wavelength obtained from a first-order kinetic model according to one example;

DETAILED DESCRIPTION

One or more embodiments of the inventive subject matter described herein employ one or more light sources generating light that inactivates pathogens with an inactivation rate that follows a kinetic dependence, or relationship, between the energy of photons of the light and the inactivation rate. In one embodiment, this kinetic energy dependence, or relationship, can provide for an inactivation rate (e.g., a rate at which pathogens are inactivated so that the pathogens are no longer able or operable to cause disease in living organisms) that increases by a factor of ten for each 0.27 to 0.44 eV increase in the photon energy of the light. Therefore, an inactivation rate that is comparable to the inactivation rate achieved using light of about 405 nm (3.06 eV) can be achieved at a wavelength of about 355 nm (3.50 eV) to about 372 nm (3.33 eV), corresponding to 0.44 to 0.27 eV increase per factor of 10 inactivation rate increase, respectively, using only about 10% of the power used for inactivating pathogens with 405 nm light. This can allow for the electrical lighting power density (LPD) used in the light source for inactivation of pathogens to be reduced (e.g., from about 12-35 $W_{el}/m^2$ to about 4 $W_{el}/m^2$ or to about 1 $W_{el}/m^2$, or another value) while increasing the efficacy of the combined illuminating and disinfecting system relative to some known visible light disinfection systems from approximately 10-30 LPW to 80 LPW or higher.

Figure 7:
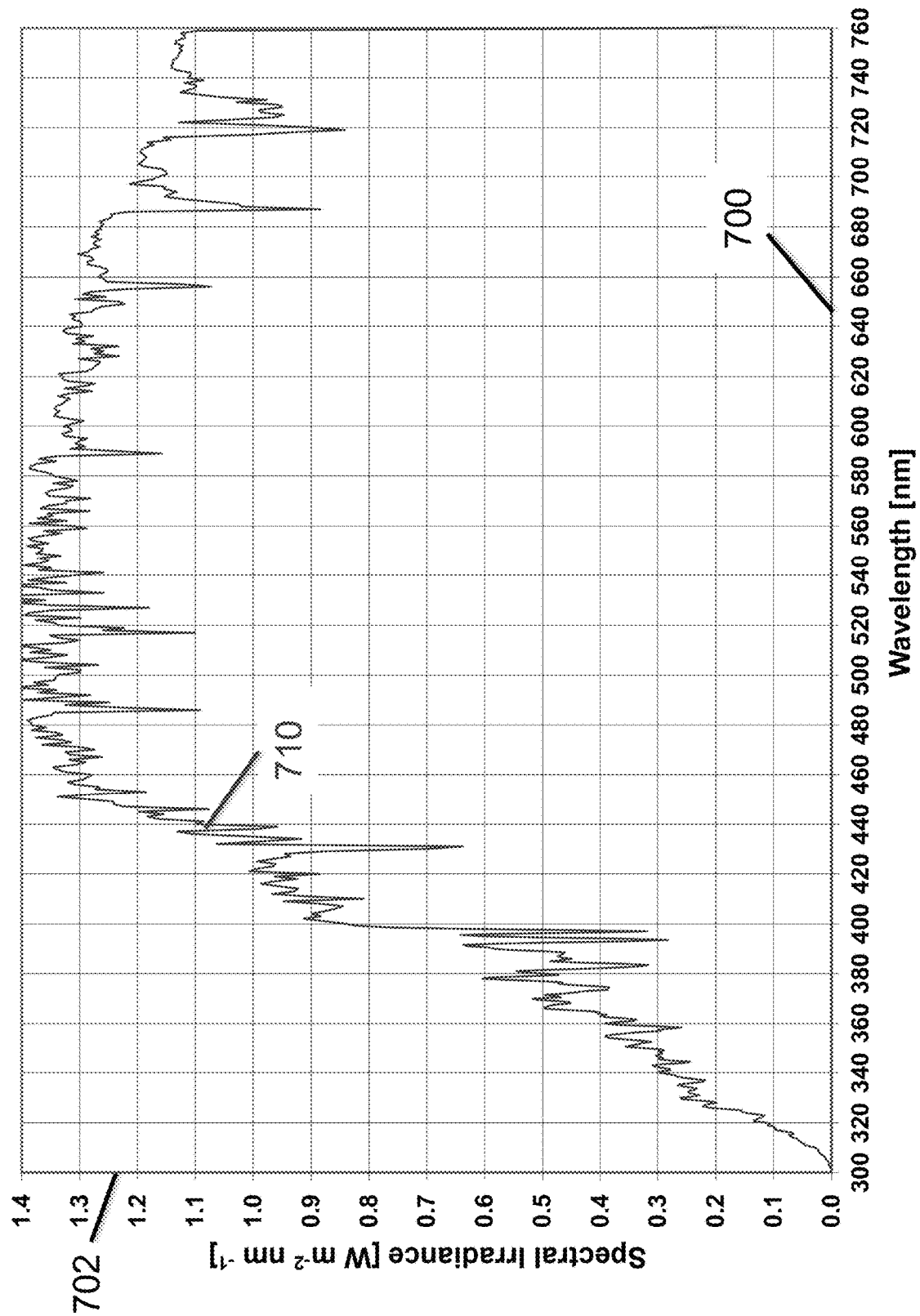
FIG. 7 illustrates total hemispherically 2π-integrated irradiance at a reasonable average for the 48 contiguous states of the United States of America over a period of one year according to one example.

To provide perspective on the scale of the irradiance in the prior art and in the present invention required to inactivate about 90-99% of common pathogens, it is useful to compare those irradiances with the irradiance of the sun. At the top of the earth's atmosphere the irradiance (integrated over all wavelengths) from the sun is about 1400 W/m², reduced to about 1100 W/m² at the earth's surface at sea level, with the sun at zenith. A standard solar irradiance spectrum has been defined by the American Society for Testing and Materials document ASTM G173-03, which is incorporated herein by reference. The Terrestrial Global 37 degree Direct Normal+ Circumsolar irradiance (i.e., total hemispherically 2π-integrated irradiance at a reasonable average for the 48 contiguous states of the United States of America over a period of one year) vs. wavelength 710 is shown in FIG. 7, and is herein referred to as "solar irradiance". Solar irradiance averages about 1.2 W/m²-nm in the visible range, and about 0.35 W/m²-nm in the UVA range. Specifically, the irradiance is about 0.88 W/m²-nm at 405 nm, and about 0.42 W/m²-nm at 365 nm. For an LED light source having a Gaussian distribution of wavelengths characterized by a peak wavelength, and a spread of wavelengths defined by the full-width at half-maximum (FWHM), with FWHM equal to about 20 nm, the solar irradiance integrated over the wavelength distribution of a 405 nm LED is about 18 W/m², and for a 365 nm LED is about 9 W/m². Therefore, the irradiance of about 4 W/m² required in the prior art to inactivate pathogens at about 405 nm is about 4× weaker than the 18 W/m² solar irradiance at the earth's surface integrated over the range of wavelengths emitted by the 405 nm LED; and the irradiance of less than 1 W/m² required in the present invention to inactivate pathogens at about 365 nm is about 9× weaker than the 9 W/m² solar irradiance at the earth's surface integrated over the range of wavelengths emitted by the LED. In this estimate, the prior art (and present invention) can be interpreted as being about 4× (and at least 9×) safer than exposure to those same wavelengths from the sun. Since continuous exposure to the sun is not considered to be safe for humans, this estimate is not sufficient to establish safety for human exposure. Rather, the actual photobiological hazard calculations will be provided in a later section. This estimate, however, does provide perspective to the relatively low irradiation that is required for 90-99% inactivation of common pathogens using violet or UVA light. Both the prior art and the present invention have been found to provide 90-99%, or more, inactivation of common pathogens using about 1 order of magnitude less irradiance using LEDs than is provided by sunlight, when integrated over the corresponding wavelength ranges.

Figure 8:
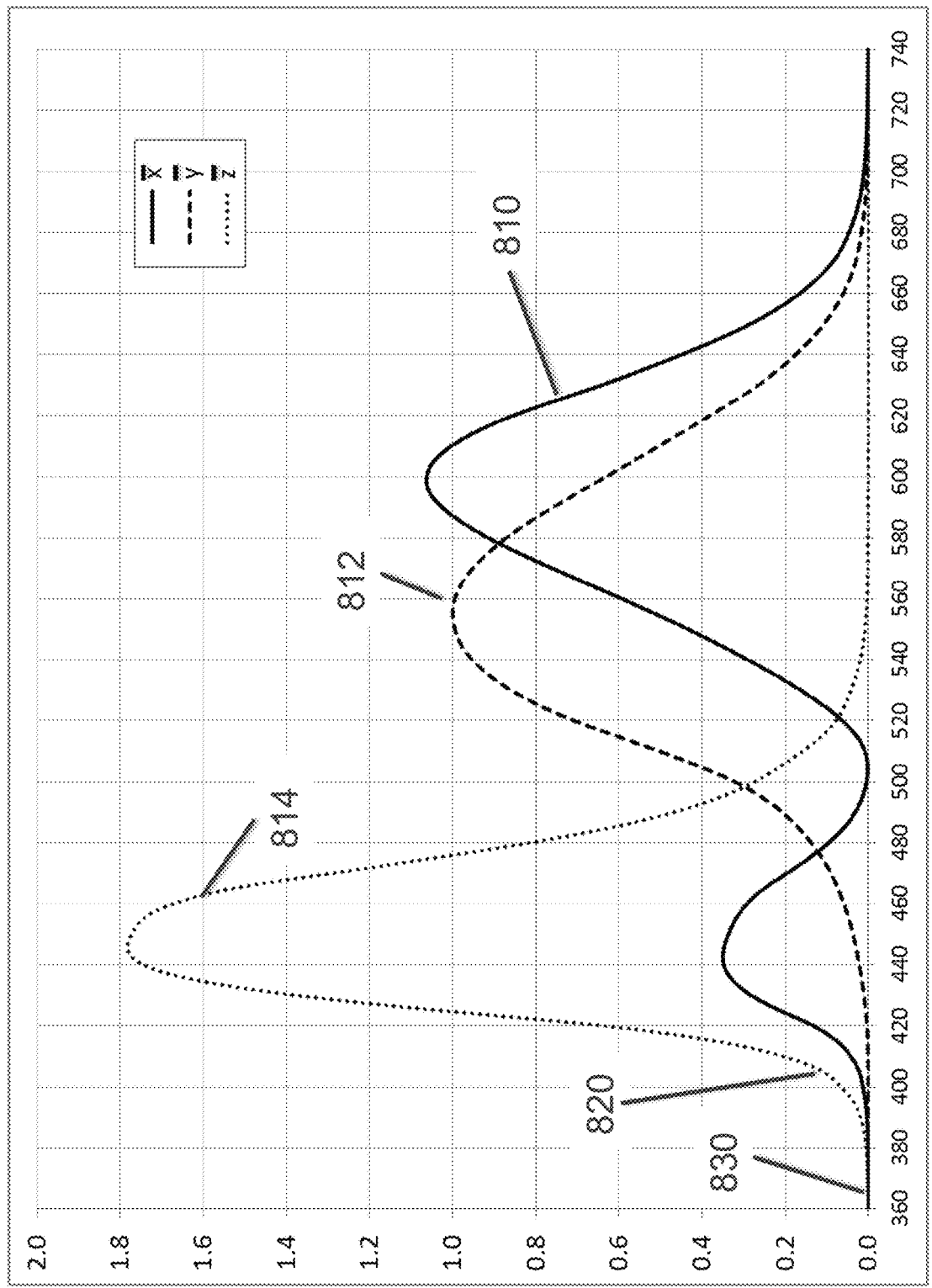
FIG. 8 illustrates the three color-matching functions according to the 1931 CIE (the International Commission on Illumination) XYZ color space.

Additionally, reducing the wavelength of light used to inactivate pathogens below about 380 nm, or a lower value, causes the inactivating portion of the light to be less perceptible to human beings or a human observer of the light. FIG. 8 illustrates the three color-matching functions—x function 810, y function 812, and z function 814—according to the 1931 CIE (the International Commission on Illumination) XYZ color space. They provide the numerical description of the chromatic response of a standard observer, from which color responses of the human eye are calculated. The strongest of the 3 functions in the violet and UVA range is the z function, which has a magnitude 820 of about 0.11 at 405 nm, but only a magnitude 830 of about 0.0011 at 365 nm, or 100 times smaller than at 405 nm. Even though some humans are known to be able to perceive light having wavelengths as short as about 310 nm, the average human perception of light having wavelengths shorter than about 380 nm is very low, and is exponentially diminishing vs. wavelength, so that the CIE standards for calculating the human perception of light is quantified to be zero at wavelengths shorter than 360 nm. Light at longer wavelengths in the violet and blue (such as 405 nm) is visible to human beings, and it is known that high flux densities of violet or blue light can cause undesirable physiological effects, including nausea, dizziness, and discomfort. Using a shorter wavelength of light as described herein may substantially reduce the distortion of the color of the illuminant and the lighted space, and the undesirable physiological effects. Optionally, the inactivating light source may be separate from the white-light source that illuminates the space, and since the relative invisibility of the inactivating light is less apparent, and less disturbing to the inhabitants, it may even be left on continuously with or without the white-light source.

Figure 3:
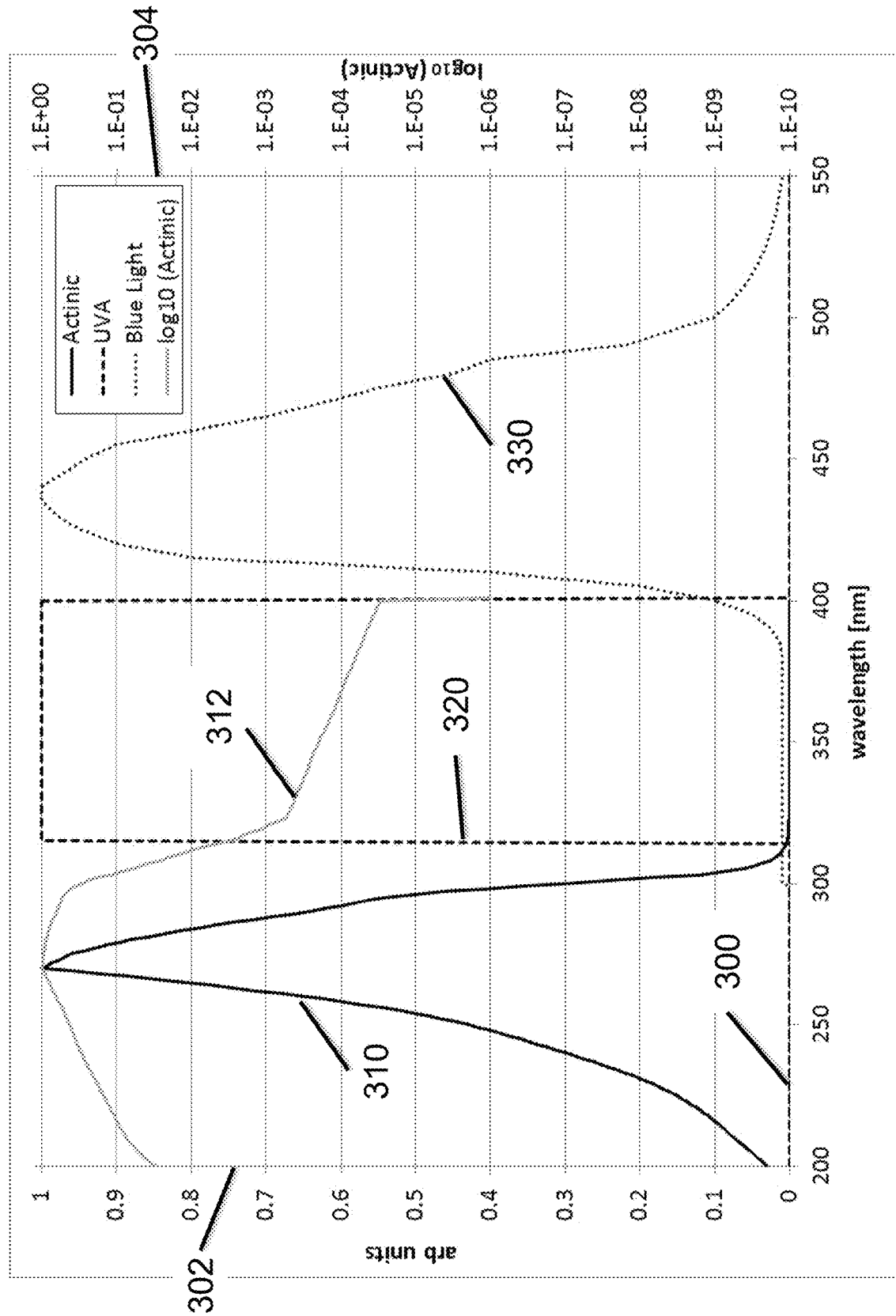
FIG. 3 illustrates several hazard functions.

An additional benefit of the shorter wavelengths of light used in one or more embodiments of the inventive subject matter described herein is that sufficient irradiance can be provided at these wavelengths to inactivate common pathogens, without exceeding safety limits for human exposure to skin or eyes. There are currently six types of photobiological hazards for optical radiation in the range 200 to 3000 nm (UV through infrared, or IR) that are covered by international standards: Actinic UV, Near UV, Blue Light, Retinal Thermal, Cornea/Lens IR, and Low Luminance Retinal IR. The first three hazards pertain to light sources emitting in the blue, violet, and UV ranges, and must be addressed in disinfection lighting systems operating in the blue, violet, or UV. A known visible light disinfection system uses a radiant power density of about 0.5 to about 5 W/m², typically about 1 W/m², of disinfecting light having a wavelength centered on about 405 nm to achieve about 90-99% inactivation of a population of common pathogens after about 5 to 10 hours of exposure is known to be safe relative to each of the three blue, violet, and UV hazards. Of the three photobiological hazards pertinent in the blue, violet, and UV ranges, as shown in FIG. 3, the UVA hazard function 320 is flat in the range 315 to 400 nm, but only the actinic hazard function 310 increases at decreasing wavelengths below 405 nm. Therefore, it has been anticipated in the prior art that a disinfection light source operating at wavelengths in the UV (i.e., below 400 nm) may be unsafe relative to the UVA or actinic hazards. While it may be true that UVC or short-wavelength UVB irradiance sufficient to inactivate pathogens is unsafe for humans, we have discovered that UVA and long-wavelength UVB radiation in a range of about 300 nm to about 400 nm that has sufficient irradiance to inactivate pathogens is safe for humans. We have discovered that the decrease in wavelength required to increase the inactivation rate of S. aureus by 10× (i.e., 1–log) at a constant dose having magnitude ~10 $J/cm^2$ is about 32 nm in the range from about 405 nm to about 365 nm. This result implies that the irradiance at 365 nm required to provide about 90-99% kill of S. aureus is about 18× lower than that required at 405 nm. Of the three relevant action spectra for photobiological hazards the hazard that increases fastest vs. decreasing wavelength is the actinic hazard, which increases by only about 3.6× from 400 nm to 365 nm. So, the radiant power density required for about 90-99% inactivation of common pathogens at 365 nm is actually about 5× (18× vs. 3.6×) safer on actinic hazard for human exposure than the radiant power density required for about 90-99% inactivation of common pathogens at 400 nm. This is exactly the opposite of the trend that is taught in prior art which states that UV light is more hazardous than visible light, and therefore using visible light for disinfection is safer for humans than using UV light. One of our discoveries is that the slope of the inactivation rate vs. wavelength greatly exceeds the slope of any of the photobiological hazard functions as the wavelength of the disinfecting light is reduced from the violet down through the UVA, and possibly even shorter wavelengths. This discovery enables the inactivation of common pathogens using UV light in the range of about 300 nm to about 400 nm with the following advantages, relative to using light in the visible range, that have not been anticipated in the prior art: higher electrical system efficiency; lower system cost; less distortion of the color point when mixed with white light; reduced or eliminated physiological disturbance to humans; greater photobiological safety for humans; higher inactivation rate of pathogens.

Figure 1:
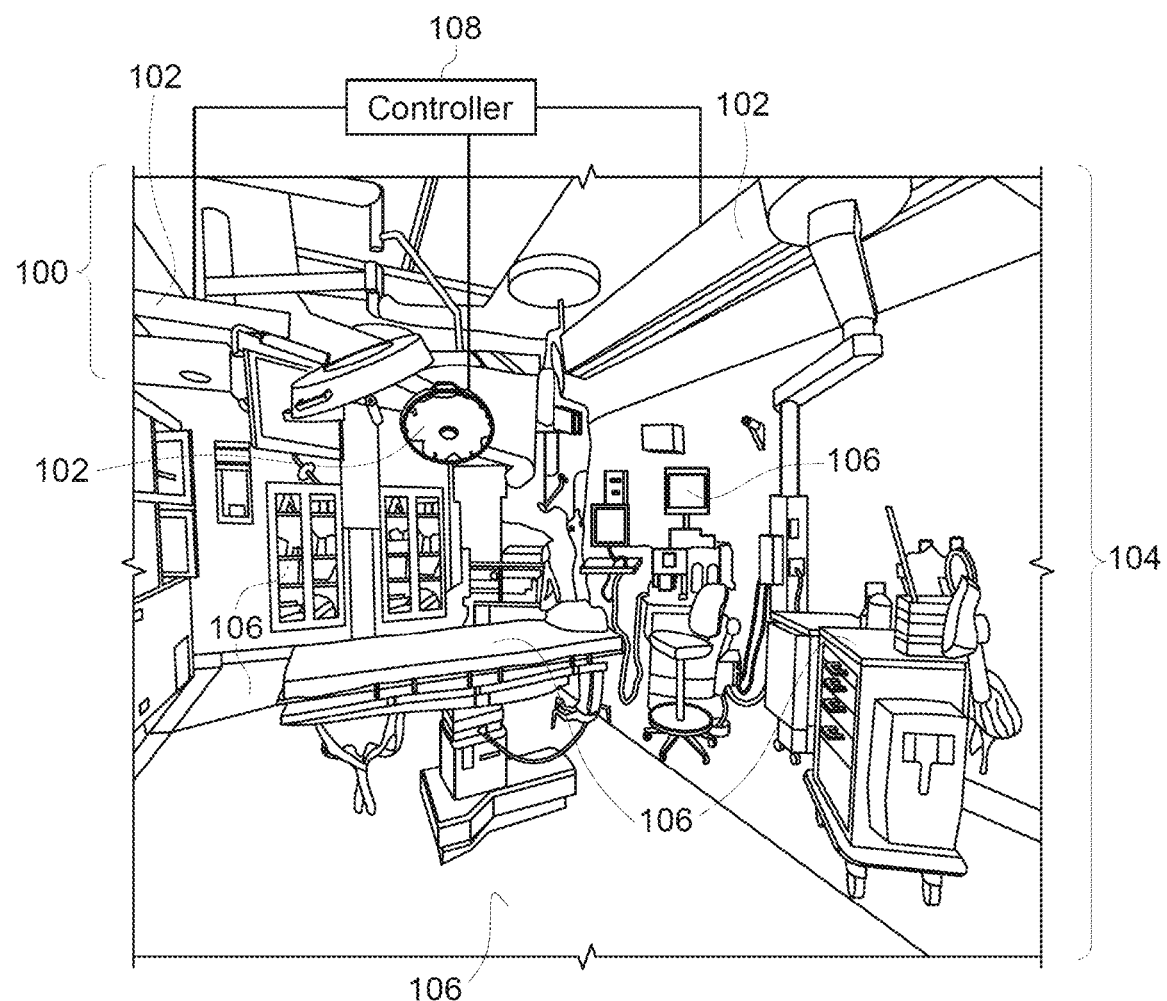
FIG. 1 illustrates a lighting system according to one embodiment of the inventive subject matter.

FIG. 1 illustrates a lighting system 100 according to one embodiment of the inventive subject matter. The system 100 includes one or more light sources 102 disposed in an environment 104 to be disinfected of pathogens. The light sources 102 may be powered from a power source (not shown in FIG. 1), such as a utility grid, batteries, etc. In the illustrated embodiment, the environment 104 is a medical surgical suite, but optionally may be another environment, such as a hospital room, a doctor's office, a dentist office, a school or room in a school, bathroom, or a public area. The light source(s) 102 may include LEDs that generate light toward one or more surfaces or materials 106 in the environment 104 to inactivate one or more pathogens on the one or more surfaces or materials 106. Alternatively, the light source(s) 102 may include one or more other devices that generate light. In one embodiment, the surfaces or materials 106 may be solid objects, and may not include water or air in one embodiment. For example, the light generated by the light source(s) 102 may inactivate pathogens on floors, walls, and solid or tangible surfaces in the environment 104.

In one embodiment, the system 100 can include one or more controllers 108 that control operation of the light source(s) 102. The controller 108 can represent hardware circuitry that includes and/or is connected with one or more processors (e.g., microcontrollers, microprocessors, field programmable gate arrays, integrated circuits, or the like) that control activation or deactivation of the light sources 102. The controller 108 can direct power and/or control signals to the light sources 102 (or drivers of the light sources 102) to control the light sources 102. In one aspect, the controller 108 may cause the light sources 102 to generate light of different wavelengths at different times. For example, the controller 108 may direct one or more of the light sources 102 to pulse the inactivating portion of the light, for example, at a frequency exceeding about 100 hertz (e.g., at least 105 hertz, at least 100 hertz, at least 90 hertz, at least 95 hertz, etc.), with a duty factor of less than about 0.5 (e.g., less than 0.6, less than 0.5, less than 0.4, etc.), or with a duty factor of less than about 0.1 (e.g., less than 0.2, less than 0.1, less than 0.05, etc.).

The pathogens that may be inactivated may include a variety of bacteria, such as staphylococcus (which may include, by way of non-limiting example, methicillin-resistant Staphylococcus aureus, or MRSA, or another type of staphylococcus), Clostridium difficile, streptococcus, bacterial pneumonia, etc., as well as some forms of spores, fungi, and viruses. The pathogens may be inactivated by killing the pathogens, rendering the pathogens unable to grow or reproduce, or generally rendering them unable to cause disease in humans.

The light source(s) 102 can generate the disinfecting light within a designated flux density range. This flux density range or power density range can be between several milliwatts per square meter ($mW/m^2$), (e.g., five $mW/m^2$ or 40 $mW/m^2$) and several watts per square meter (e.g., two or three or ten $W/m^2$). In one embodiment, the flux density range extends upward to no more than 10 $W/m^2$. Alternatively, the flux density range can be in another range. The light generated by the light source(s) 102 may have several different wavelengths, with a portion of the light being inactivating light having wavelengths that inactivate the pathogens and one or more other portions of the light having other, different wavelengths. This inactivating portion of the light may be invisible to human beings. For example, the inactivating portion of the light may have a wavelength that is no longer than 380 nm. As described below, the inactivating portion of the light may have a lower limit on the wavelength of light to avoid exposing human beings to hazardous radiation. For example, the inactivating portion of the light may have a wavelength that is at least 280 nm, or at least 300 nm, or at least 320 nm, or another lower limit.

At shorter wavelengths of light (e.g. UVB and UVC) used by other lighting systems, pathogens may be lethally inactivated by permanently breaking deoxyribonucleic acid (DNA) or ribonucleic acid (RNA) macromolecules of the pathogens. At the longer wavelengths (e.g. UVA), the inactivating portion of the light generated by the light source(s) 102 may inactivate the pathogens by catalyzing chemical surface reactions on exterior surfaces such as the cell membrane; or by causing single-strand DNA breaks which may be non-lethal; or by damaging less robust intracellular structures of the bacteria, resulting in sublethal effects such as growth reduction, reduction of bacterial capacity for phage development, inhibition of induced-enzyme (tryptophanase) synthesis, inhibition of membrane transport, and other non-lethal damage which may be repaired by the cell at low doses, but which accumulate at higher doses resulting in damage levels that inactivate the cell or significantly reduce the growth of the cell so as to effectively inactivate the cell. There exist a large number of potential target chromophores (the part of a given molecule in the cell that absorbs certain wavelengths of light and transmits or reflects others) in any given pathogenic cell, each chromophore potentially having a specific range of absorbing wavelengths which may differ from other chromophores, and resulting in different photo-products due to the energy exchange from the chromophore to other molecules in the cell, resulting in disruption of the normal chemical processes in the cell. Whereas, the breaking of DNA molecules by high-energy UVC is known to have a strong resonance between about 240 nm and 280 nm; and whereas it is believed that at about 405 nm, the photoexcitation of naturally occurring endogenous porphyrins on the surface of the cell, which act as endogenous photosensitizers within the cells leads to energy transfer and, ultimately, the production of highly cytotoxic, oxygen-derived species, leading to cell damage or death; the mechanisms of cell damage in the UVA range is believed to be many and varied, not represented by any single resonance band of wavelengths. In this wavelength regime, having a large number of potential chromophores and resonance wavelength bands in any given cell, it may be reasonable to hypothesize that the rate at which the pathogens are inactivated by the inactivating portion of the light generated by the light source(s) 102 (which also can be referred to as a kill or inactivation rate) may be significantly faster for higher energy photons than for lower energy photons. The rate at which the pathogens are inactivated by UVA radiation may be hypothesized to be based on a first-order kinetic relationship, or equivalently, the Arrhenius equation. The inactivation rate of the inactivating portion of the light may be hypothesized to increase exponentially as the photon energy of the inactivating portion of the light increases, with the photon energy being inversely related to the wavelength of light. As a result, the inactivation rate of the inactivating portion of the light may exponentially increase as the wavelength of the inactivating portion of the light decreases.

A first-order kinetic model for the inactivation rate as a function of photon energy may be hypothesized by analogy to the first-order kinetic model for inactivation as a function of temperature used in the food processing industry as provided by Equation 5 in the reference titled "Safe Practices for Food Processes>Kinetics of Microbial Inactivation for Alternative Food Processing Technologies Overarching Principles: Kinetics and Pathogens of Concern for All Technologies, published by the U.S. Food and Drug Administration, last updated on Apr. 9, 2013, herein incorporated by reference, and referred to as 2013 FDA. In this analogy, the temperature variable in the 2013 FDA model is replaced with photon energy for the hypothesis herein that relates inactivation rate or dose to photon energy. In 2013 FDA, the influence of temperature on microbial population inactivation rates has been expressed in terms of the thermal resistance constant z(T) using the following model:

$$\log_{10}[D/D_R] = -(T-T_R)/z(T) \quad \text{Equation 5 in 2013 FDA}$$

where D is the decimal reduction time, or time required for a $1$-$\log_{10}$ ($10\times$) cycle reduction in the microbial population; the thermal resistance constant z(T) is the temperature increase needed to accomplish a $1$-$\log_{10}$ cycle reduction in D; the reference decimal reduction time $D_R$ is the magnitude at a reference temperature $T_R$ within the range of temperatures used to generate experimental data. The analogy made herein is represented in Table 1.

TABLE 1

| Variable in the Model | 2013 FDA Model | One Model Of The Inventive Subject Matter |
|---|---|---|
| Dose of inactivation energy to the pathogen population | temperature * exposure time (T*t) i.e., time at temperature | photon energy * photon flux * exposure time (E*Φ*t) i.e., time at irradiance |
| D | time at temperature required for $1$-$\log_{10}$ ($10\times$) reduction in pathogen population at the test temperature T | time at irradiance required for $2$-$\log_{10}$ ($100\times$) reduction in pathogen population at the energy E of the test photon |
| $D_R$ | time at temperature required for $1$-$\log_{10}$ ($10\times$) reduction in pathogen population at the reference temperature $T_R$ | time at irradiance required for $2$-$\log_{10}$ ($100\times$) reduction in pathogen population at the energy E of the reference photon |
| Test Energy | T, test temperature | E, energy of the test photon |
| Reference Energy | $T_R$, reference temperature | $E_R$, energy of the reference photon |
| Characteristic Energy | z(T), increase in temperature needed to accomplish a $1$-$\log_{10}$ reduction in D | z(E), increase in the energy of the disinfecting photons needed to accomplish a $1$-$\log_{10}$ reduction in D |

The dose vs. wavelength obtained by hypothesizing a first-order kinetic model is given by:

$$\log_{10}(D/D_R) = -\frac{E - E_R}{z(E)}, \quad \text{Equation 1}$$

where D is the dose required for a target (e.g. 90% or 99% or other) reduction in pathogen count using disinfecting photons of energy E; $D_R$ is the dose required for the same target reduction in pathogen count using photons of reference energy $E_R$; z(E) is the increase in photon energy needed to accomplish a 1-log (90%) reduction in D. Taking the first derivative of Equation 1 with respect to E provides $$\frac{d\log_{10}(D)}{dE} = -1/z(E). \quad \text{Equation 2}$$

So, a first-order kinetic model would be represented by a linear slope having value $-1/z(E)$ in a plot of $\log_{10}$(dose, D) on the y axis vs. photon energy E on the x axis. A steeper slope $-1/z(E)$ indicates a stronger dependence of dose of the disinfection lighting (in J/m$^2$) vs. photon energy (in eV), at some target inactivation (e.g. 90% or 99% or other).

Figure 2A:
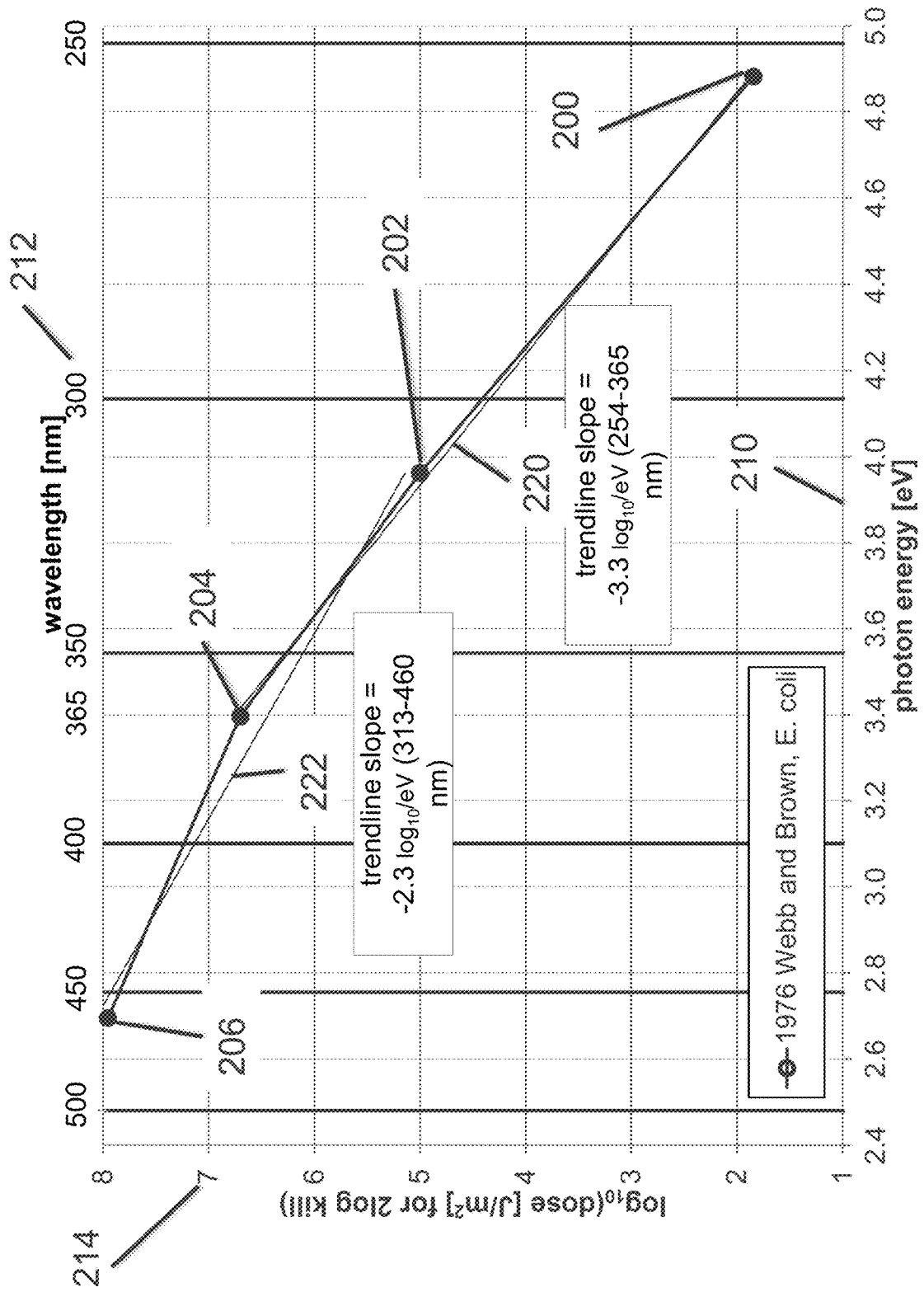
FIG. 2*a* illustrates a dataset of a dose of disinfecting light required for about 99% inactivation of *E. coli* pathogens according to one example.

FIG. 2a illustrates a dataset 200, 202, 204, 206 of the dose of disinfecting light required for about 99% inactivation of E. coli pathogens, wherein the light has a narrow spectral width (FWHM<about 20 nm), with peak emission at four different wavelengths of light (254, 313, 365, and 460 nm, respectively) according to the reference 1976 Webb and Brown (Photochemistry and Photobiology, 24:425-432, 1976). The data 200, 202, 204, 206 represent the accumulated doses at which the pathogens are inactivated by 99% ($2$-$\log_{10}$) relative to the controls which were not dosed, where the first horizontal axis 210 represents the energy of photons of the light (in electron volts, or eV) at the wavelength of peak emission, and the second horizontal axis 212 represents the wavelengths of the inactivating portions of the light (in nm) at the emission peak, and a vertical axis 214 represents the common logarithm (also known as the decimal log, or base-10 log, or $\log_{10}$) of the dose of disinfecting light required for about 99% inactivation (in terms of Joules per square meter, $J/m^2$). A linear trend line fit 220 to the subset of the data 200, 202, and 204; and a linear trend line fit 222 to the subset of the data 202, 204, and 206 also are shown. The trend line 220 represents a logarithmic relationship between the photon energy and the dose of disinfecting light, having a slope of $-1/z(E)=-3.3 \log_{10}$ per eV of photon energy in the range of about 3.4 to about 4.9 eV, corresponding to wavelengths from about 254 to about 365 nm. The trend line 222 represents a logarithmic relationship between the photon energy and the dose of disinfecting light, having a slope of $-1/z(E)=-2.3 \log_{10}$ per eV of photon energy in the range of about 2.7 to about 3.9 eV, corresponding to wavelengths from about 313 to about 460 nm. It would be expected that the trend line slope that applies in the range of about 405 to about 365 nm (i.e., the range between a typical violet-light disinfection system having peak emission at about 405 nm, and an embodiment of the present invention having peak emission at about 365 nm) should be bracketed by the slopes of the two trend lines in FIG. 2a (i.e., $-1/z(E)=-3.3 \log_{10}$ and $-1/z(E)=-2.3 \log_{10}$ per eV). It is reasonable to expect that the trend line slope that applies in the range of about 405 to about 365 nm is about equal to the average of those two slopes, or about $-1/z(E)=-2.8 \log_{10}$ per eV for 99% inactivation of E. coli. Given a slope of $-1/z(E)=2.8 \log_{10}$ per eV, the ratio of dose required for 99% inactivation of E. coli using narrow-band light having peak emissions at about 365 nm (3.40 eV) and about 405 nm (3.06 eV) is $10^{2.8*(3.40-3.06)}=8.7$. From FIG. 2a, it is expected that the dose of disinfecting light required for about 99% inactivation of E. coli may be reduced by about 8.7× when the wavelength is reduced from about 405 nm to about 365 nm. A greater (lesser) ratio would be expected at wavelengths shorter (longer) than about 365 nm, compared with about 405 nm.

Figure 2B:
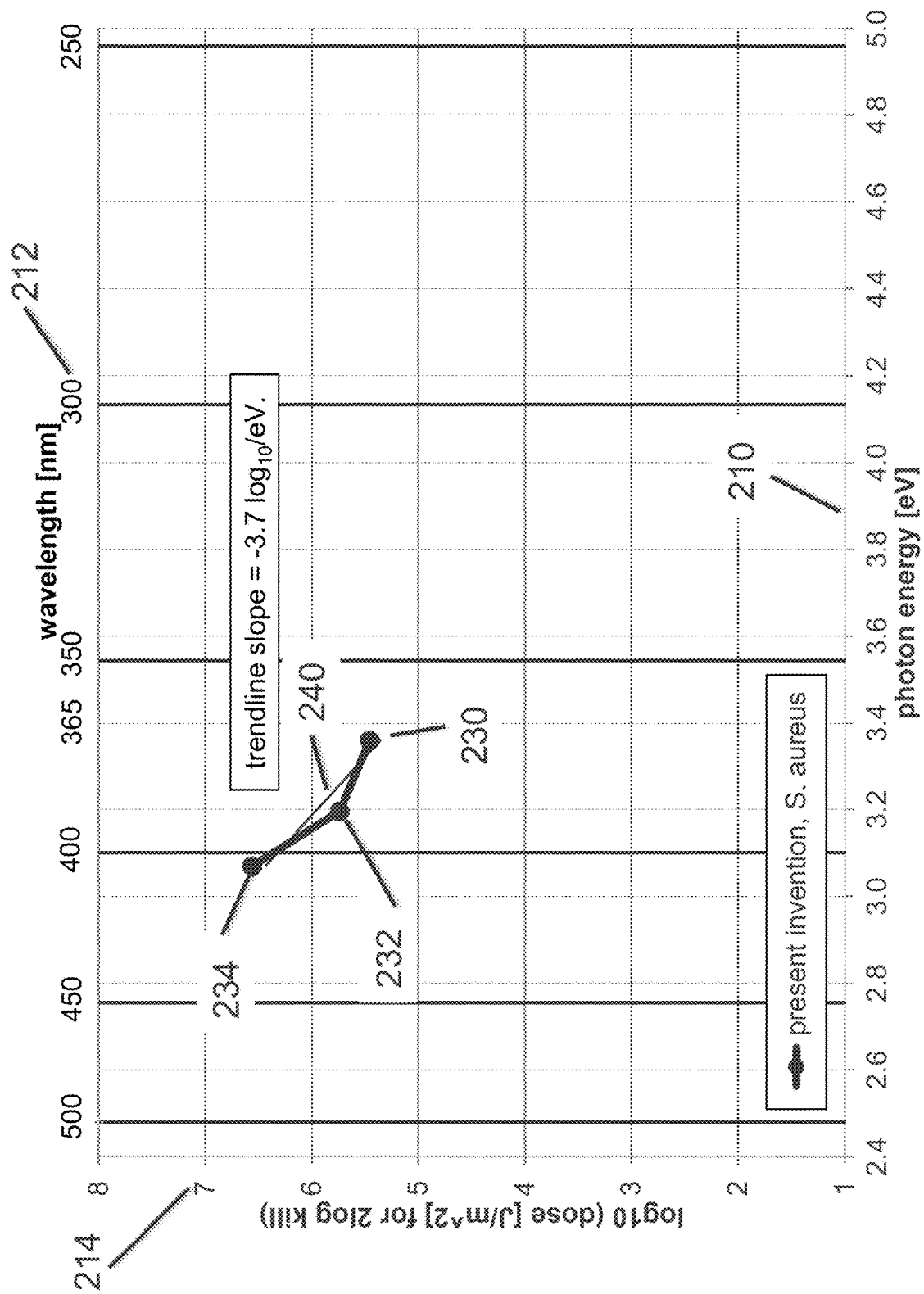
FIG. 2*b* illustrates a dataset of a dose of disinfecting light required for about 99% inactivation of *S. aureus* pathogens according to one embodiment of the inventive subject matter.

FIG. 2b illustrates a dataset 230, 232, 234 of the dose of disinfecting light required for about 99% inactivation of S. aureus pathogens, wherein the disinfecting light is provided by LEDs having a narrow spectral width (FWHM<about 20 nm), with peak emission at three different wavelengths of light (369, 388, and 404 nm, respectively) according to the present invention. A linear trend line fit 240 to the data 230, 232, and 234 also is shown. The data 230, 232, 234 represent the accumulated dose at which the pathogens are inactivated by 99% ($2-\log_{10}$) relative to the controls which were not dosed, where the first horizontal axis 210 represents the energy of photons of light, and the second horizontal axis 212 represents the wavelengths of the inactivating portions of the light (in nm), and a vertical axis 214 represents the $\log_{10}$ of the accumulated dose of disinfecting light (in $J/m^2$). The inactivation trend line 240 represents a logarithmic relationship between the photon energy and the dose, having a slope of $-1/z(E)=-3.7 \log_{10}$ per eV of photon energy in the range of about 3.0 to about 3.4 eV, corresponding to wavelengths from about 369 to about 404 nm. These data were obtained using commercially available LEDs having measured peak wavelengths of 369, 388, and 404 nm, which were labeled by the manufacturers as having nominal peaks at 365, 390, and 405 nm, respectively. This variance between measured and labeled wavelength is typical for commercially available LEDs which are typically binned within +/−5 nm ranges. It would be expected that the trend line slope that applies in the range of about 405 to about 365 nm (i.e., the range between a typical violet-light disinfection system with peak emission at about 405 nm, and an embodiment of the present invention with peak at about 365 nm) should be bracketed by the slopes of the two trend lines in FIG. 2a (i.e., $-1/z(E)=-3.3 \log_{10}$ per eV and $-1/z(E)=-2.3 \log_{10}$ per eV; the average of the two slopes is about $-1/z(E)=-2.8 \log_{10}$ per eV). In fact, the trend line 240 fitting the data of the present invention is about $-1/z(E)=-3.7 \log_{10}$ per eV, exceeding the expected range of slopes from the prior art data in FIG. 2a. Given a slope of $-1/z(E)=-3.7 \log_{10}$ per eV, the ratio of dose required for 99% inactivation of S. aureus using narrow-band light having peak emissions at about 405 nm (3.06 eV) relative to dose required at about 365 nm (3.40 eV) is $10^{3.7*(3.40-3.06)}=17.4$. From FIG. 2b, it is expected that the dose of disinfecting light required for about 99% inactivation of S. aureus may be reduced by about 17.4× when the wavelength is reduced from about 405 nm to about 365 nm. A greater (lesser) ratio would be expected at wavelengths shorter (longer) than about 365 nm, when compared with about 405 nm. This beneficial ratio of doses at 365 nm vs. 405 nm having a value of about 17.4 is unexpectedly, significantly greater than the 8.7 ratio of doses anticipated from the prior art. Even though the data in FIG. 2a pertain to E. coli, while that in FIG. 2b pertains to S. aureus, it is the wavelength dependence of the required dose that we are investigating, not the relative dose required between the two different pathogens.

Figure 2D:
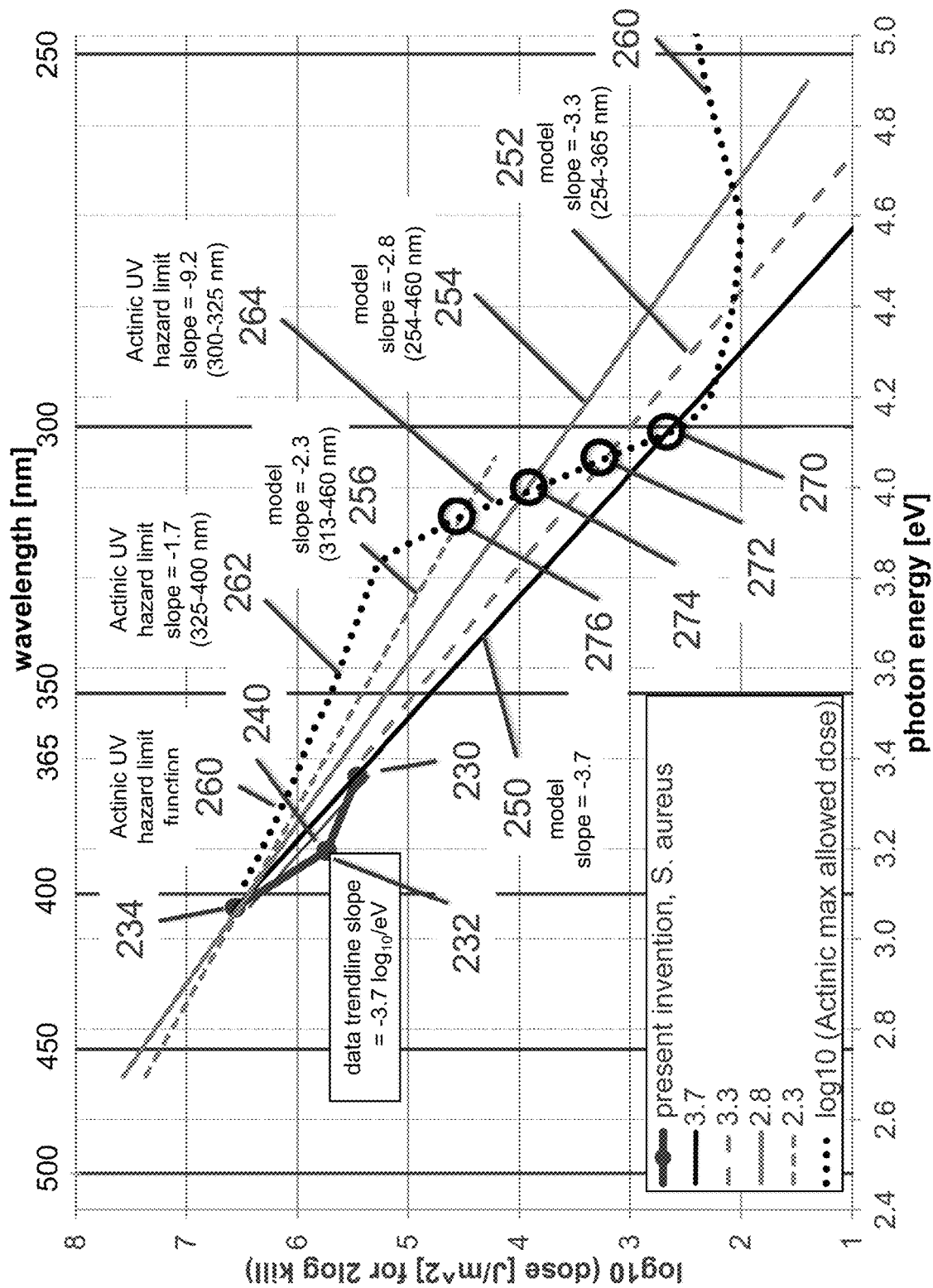
FIG. 2*d* illustrates the dataset with the linear trend line fit from FIG. 2*b* with the lines from FIG. 2*c* according to one example.

FIG. 2c illustrates the dataset 230, 232, 234, including the linear trend line fit 240, from FIG. 2b, along with the four lines 250, 252, 254, 256 representing the dose vs. wavelength obtained from the first-order kinetic model of Equation 1, corresponding to characteristic energies, $-1/z(E)=-3.7, -3.3, -2.8, -2.3 \log_{10}$ per eV, respectively. The line 250 represents the dose vs. energy relationship expected from Equation 1 where $-1/z(E)=-3.7 \log_{10}$ per eV corresponding to the trend line fit to the data 230, 232, 234 of the present invention; the line 252 represents the dose vs. energy relationship expected from Equation 1 where $-1/z(E)=-3.3 \log_{10}$ per eV corresponding to the trend line fit to the data 200, 202, 204 of the reference 1976 Webb and Brown; the line 256 represents the dose vs. energy relationship expected from Equation 1 where $-1/z(E)=-2.3 \log_{10}$ per eV corresponding to the trend line fit to the data 202, 204, 206 of the reference 1976 Webb and Brown; the line 254 represents the dose vs. energy relationship expected from Equation 1 where $-1/z(E)=-2.8 \log_{10}$ per eV corresponding to the average of the trend line fit to the data 200, 202, 204, and the trend line fit to the data 202, 204, 206 of the reference 1976 Webb and Brown. The line 254 represents the most likely trend line pertaining to the wavelength range from about 405 nm to about 365 nm for the data 200, 202, 204, 206 from the reference 1976 Webb and Brown. FIG. 2d illustrates the dataset 230, 232, 234, including the linear trend line fit 240, from FIG. 2b; along with the four lines 250, 252, 254, 256 from FIG. 2c, representing the dose vs. wavelength obtained from the first-order kinetic model of Equation 1, corresponding to trendline fits, $-1/z(E)=-3.7, -3.3, -2.8, -2.3 \log_{10}$ per eV, respectively; along with a plot 260 of the maximum allowed dose vs. photon energy according to the Actinic UV photobiological hazard function, normalized to match the dose 234 at about 400 nm, having a first slope 262 of $-1.7 \log_{10}$ per eV in the range from about 3.1 eV to about 3.8 eV (about 400 nm to about 325 nm) and having a second slope 264 of $-9.2 \log_{10}$ per eV in the range from about 3.8 eV to about 4.1 eV (about 325 nm to about 300 nm). Since the Actinic UV hazard function 260 is normalized to the dose 234 at 400 nm, and the slopes of each of the first-order kinetic model curves 250, 252, 254, 256 exceed the slope 262 (−1.7 $\log_{10}$ per eV) of the curve 260 in the range 325 to 400 nm, then the safety margin between the dose required for 99% disinfection of *S. aureus* and the maximum dose permitted by the Actinic UV hazard function increases as the wavelength of the disinfecting light decreases from 400 nm to 325 nm. This increasing margin of safety vs. decreasing wavelength at wavelengths below 400 nm is the opposite trend that is expected from the prior art. At wavelengths shorter than about 325 nm, the slope 264 of the Actinic UV hazard function 260 increases sharply to about −9.2 $\log_{10}$ per eV, greatly exceeding the slopes of each of the first-order kinetic model curves 250, 252, 254, 256, so that the margin of safety vs. decreasing wavelength at wavelengths below about 325 nm diminishes rapidly. The relative margin of safety becomes one at the intersection of the Actinic UV hazard function 260 with each of the first-order kinetic model curves 250, 252, 254, 256 at the circles 270, 272, 274, 276, respectively, corresponding to photon energies of about 4.12, 4.05, 4.00, 3.95 eV, respectively, and wavelengths of about 301, 306, 310, 314 nm, respectively. This relatively narrow range of intersection wavelengths in the range from about 301 nm to about 314 nm, or approximately 300 nm to 315 nm, emphasizes that the actual value of the slope of the first-order kinetic model is not critical, as long as it exceeds the slope 262 (−1.7 $\log_{10}$ per eV) of the Actinic UV hazard function 260 in the range 325 nm to 400 nm. So, if the first-order kinetic model for 99% disinfection of *S. aureus* has a slope that is steeper than −1.7 $\log_{10}$ per eV, then the safety margin will increase down to about 325 nm, and possibly a somewhat shorter wavelength. The slope 264 (−9.2 $\log_{10}$ per eV) of the Actinic UV hazard function 260 increases so sharply at less than 325 nm, that the intersection wavelength occurs at wavelengths only slightly less than 325 nm for any kinetic model having a slope much less steep than the slope 264 (−9.2 $\log_{10}$ per eV) of the Actinic UV hazard function 260 in the range 300 to 325 nm. At any wavelength having a safety margin>1 (i.e., in the range from 400 nm down to about 300 to 315 nm), the dose of disinfecting light required for 99% inactivation of *S. aureus* is safer for humans than the dose of disinfecting light at 400 nm that is required for 99% inactivation of *S. aureus*. This is contrary to the expectations proposed in the prior art. For example, the dose of disinfecting light required for 99% inactivation of *S. aureus* at about 365 nm is about 0.67−log 10 (about 4.7×) safer for humans than the dose of disinfecting light at 400 nm, using the slope 250 (−3.7 $\log_{10}$ per eV) of the model that is the best fit to the data 230, 232, 234 of the present invention. Using the more conservative slope 256 (−2.3 $\log_{10}$ per eV) of reference 1976 Webb and Brown, the dose of disinfecting light required for 99% inactivation of *E. coli* at about 365 nm is about 0.37−log 10 (about 2.4×) safer for humans than the dose of disinfecting light at 400 nm. Similar trends and conclusions may be expected for disinfection levels exceeding 90-99%, as well. The safety margins increase vs. decreasing wavelengths down to about 325 nm, and then decline to <1 in the range of about 300 to 315 nm, as shown in Table 2.

TABLE 2

| Wavelength of disinfecting light [nm] | Safety margin for 99% disinfection of *S. aureus* @ −3.7 $\log_{10}$ per eV | Safety margin for 99% disinfection of *E. coli* @ −2.3 $\log_{10}$ per eV |
|---|---|---|
| 405 | 1.0 | 1.0 |
| 385 | 2.1 | 1.5 |
| 365 | 4.7 | 2.4 |

TABLE 2-continued

| Wavelength of disinfecting light [nm] | Safety margin for 99% disinfection of *S. aureus* @ −3.7 $\log_{10}$ per eV | Safety margin for 99% disinfection of *E. coli* @ −2.3 $\log_{10}$ per eV |
|---|---|---|
| 345 | 12 | 3.9 |
| 325 | 29 | 6.5 |
| 305 | 1.6 | <1 |

As shown above, reducing the wavelength of the inactivating portion of the light below about 400 nm, and especially below about 380 nm, is unexpectedly safer with regard to the Actinic UV photobiological hazard than disinfecting pathogens with light at about 400 nm, or in. Considering the other two of the three hazards that pertain to light sources emitting in the blue, violet, and UV ranges, FIG. 3 illustrates all three hazard functions: the Actinic UV 310, Near UV 320, and Blue Light 330 hazards. The $\log_{10}$(Actinic UV) curve 312 is also illustrated in FIG. 3. The hazard functions 310, 320, 330 are shown alongside a horizontal axis 300 representative of wavelengths of light and a vertical axis 302 representative of the risk posed by exposure to the light as a function of the wavelength of the light source. The Actinic UV hazard has been shown above to be unexpectedly less hazardous for wavelengths in the range from about 315 nm to about 380 nm than for longer wavelengths in the range from about 380 nm to about 400 nm at doses required to inactivate pathogens at the 90-99% level. The additional two photobiological hazards are, as expected from the spectral shapes of the hazard functions, not any more hazardous in the 315-380 nm range than in the 380-400 nm range at doses required to inactivate pathogens at the 90-99% level. The hazard function 312 is shown alongside a horizontal axis 300 representative of wavelengths of light and a second vertical axis 304 representing the common logarithm ($\log_{10}$) of the Actinic UV hazard function. Larger values along the vertical axis 304 represent greater health hazards than smaller values. All hazard values are normalized to 1.0. The maximum allowable emission from a light source, with regard to each photobiological hazard is determined from the convolution integral of the spectral power distribution (SPD) of irradiance of the light source (in W/m²-nm) with the hazard function, integrated over all wavelengths. The calculation is typically performed as a sum-product of the SPD and the hazard function, with each factor discretized in 1 nm or 2 nm or 5 nm increments. Herein, the sum-products are calculated with 1 nm discretization. The integral or sum-product must be less than the maximum allowable limit for each hazard. The allowable limits for Exempt and Low Risk light sources as specified by IEC 62471 are shown in Table 3a:

TABLE 3a

| Hazard | Exempt Limit | Low Risk Limit |
|---|---|---|
| Actinic UV | 30 J/m² within any 30,000 second period (equivalent to 0.001 W/m²) | 30 J/m² within any 10,000 second period (equivalent to 0.003 W/m²) |
| UVA | 10 W/m² for exposures > 1000 seconds | 33 W/m² for exposures > 300 seconds |
| Blue Light | 100 W/m²sr for exposures > 10,000 seconds | 10,000 W/m²sr for exposures > 100 seconds |

The hazard function 330 can be referred to as a blue light hazard function, as it represents the risk to humans posed by exposure to wavelengths of blue (and violet, and some UV) light. The risk represented by the hazard function 330 is maximum (1.0 value) between 435 nm and 440 nm; is very high (>0.5 value) between about 410 nm and about 480 nm; is low (<0.1 value) below 400 nm and above 500 nm; and is extremely low (0.01 value) between 300 nm and 380 nm. Therefore, the blue light hazard which poses significant risk in prior art disinfection systems operating in the range of about 380 nm to about 420 nm, is diminishingly small at wavelengths below about 380 nm. The hazard function 320 can be referred to as a UVA hazard function, since it represents risks to humans posed by exposure to wavelengths of light in the UVA band. The hazard function 320 is flat (1.0 value) between 315 nm and 400 nm, and zero outside that range. Other disinfection lighting systems operating at about 405 nm having a FWHM of about 10 nm emits about 10% of its light within the UVA range, and so is typically safe at emission levels sufficient for disinfecting pathogens. The disinfection lighting system of the present invention, with peak emission in the UV range from about 300 nm to about 380 nm, could be unsafe with regard to the Near UV hazard if the emission in the UV range is made as strong as the emission of the prior art disinfection lighting systems having peak emission at about 405 nm, but since the slope 240 (−1/z(E)=3.7 $\log_{10}$ per eV) corresponding to the trend line fit to the data 230, 232, 234 of the present invention is so steep, where the Near UV hazard function is flat, that any wavelength below about 380 nm will provide sufficient disinfection lighting without exceeding the Near UV hazard limit. Overall, it has been found, unexpectedly, that the dose of disinfection light required to inactivate about 90-99% of pathogens using narrow-band light having peak emission in the range from about 300 nm to about 380 nm has margins of safety relative to the three photobiological hazards pertaining to this part of the spectrum that are comparable to, or safer than, the margins of safety for 90-99% disinfection of pathogens using narrow-band light having peak emission in the range of about 380 nm to 420 nm. The safety margins provided by the prior art and by this invention are summarized in Tables 3b and 3c for a dose of disinfection light sufficient to provide 90% and 99% kill, respectively, of S. aureus over a period of 8 hours. The safety factors presented in tables 3b and 3c are relative to the Exempt hazard limit. Safety factors would be higher in all cases relative to the Low Risk limit.

TABLE 3b

90% disinfection of S. aureus

| Hazard | Exempt Limit | Other Systems Peak at 405 nm 55 J/cm² | | Inventive Subject Matter Peak at 365 nm 11 J/cm² | | Inventive Subject Matter Peak at 325 nm 0.3 J/cm² | |
|---|---|---|---|---|---|---|---|
| | | Result | Margin | Result | Margin | Result | Margin |
| Actinic UV | 0.001 W/m² | 0.0001 | 10 | 0.0004 | 2.5 | 0.00018 | 5.4 |
| UVA | 10 W/m² | 2.9 | 3.4 | 3.7 | 2.7 | 0.10 | 87 |
| Blue Light | 100 W/m²sr | 87 | 1.2 | 4.3 | 23 | 3.6 | 28 |
| Du'v' | | 0.236 | | 0.003 | | 0.000 | |

TABLE 3c

99% disinfection of S. aureus

| Hazard | Exempt Limit | Prior art Peak at 405 nm 109 J/cm² | | Inventive Subject Matter Peak at 365 nm 21.4 J/cm² | | Inventive Subject Matter Peak at 325 nm 0.7 J/cm² | |
|---|---|---|---|---|---|---|---|
| | | Result | Margin | Result | Margin | Result | Margin |
| Actinic UV | 0.001 W/m² | 0.00020 | 5.1 | 0.00080 | 1.2 | 0.00037 | 2.7 |
| UVA | 10 W/m² | 5.8 | 1.7 | 7.4 | 1.4 | 0.23 | 43.8 |
| Blue Light | 100 W/m²sr | 170 | 0.6 | 5 | 19.3 | 3.6 | 27.8 |
| Du'v' | | 0.317 | | 0.006 | | 0.000 | |

Table 3b indicates that disinfection lighting sufficient to provide about 90% inactivation of S. aureus is safe relative to all three of the relevant photobiological hazards for 405, 365, and 325 nm. It shows that while the 405 nm disinfection lighting is only marginally safe relative to the Blue Light Hazard, the 325 nm and 365 nm disinfection lighting have high safety margins relative to all three hazards.

Table 3c indicates that disinfection lighting sufficient to provide about 99% inactivation of S. aureus is safe relative to all three of the relevant photobiological hazards only for 325 nm and 365 nm. It shows that the 405 nm disinfection lighting can become unsafe relative to the Blue Light Hazard, if higher disinfection levels are desired.

Figure 9A:
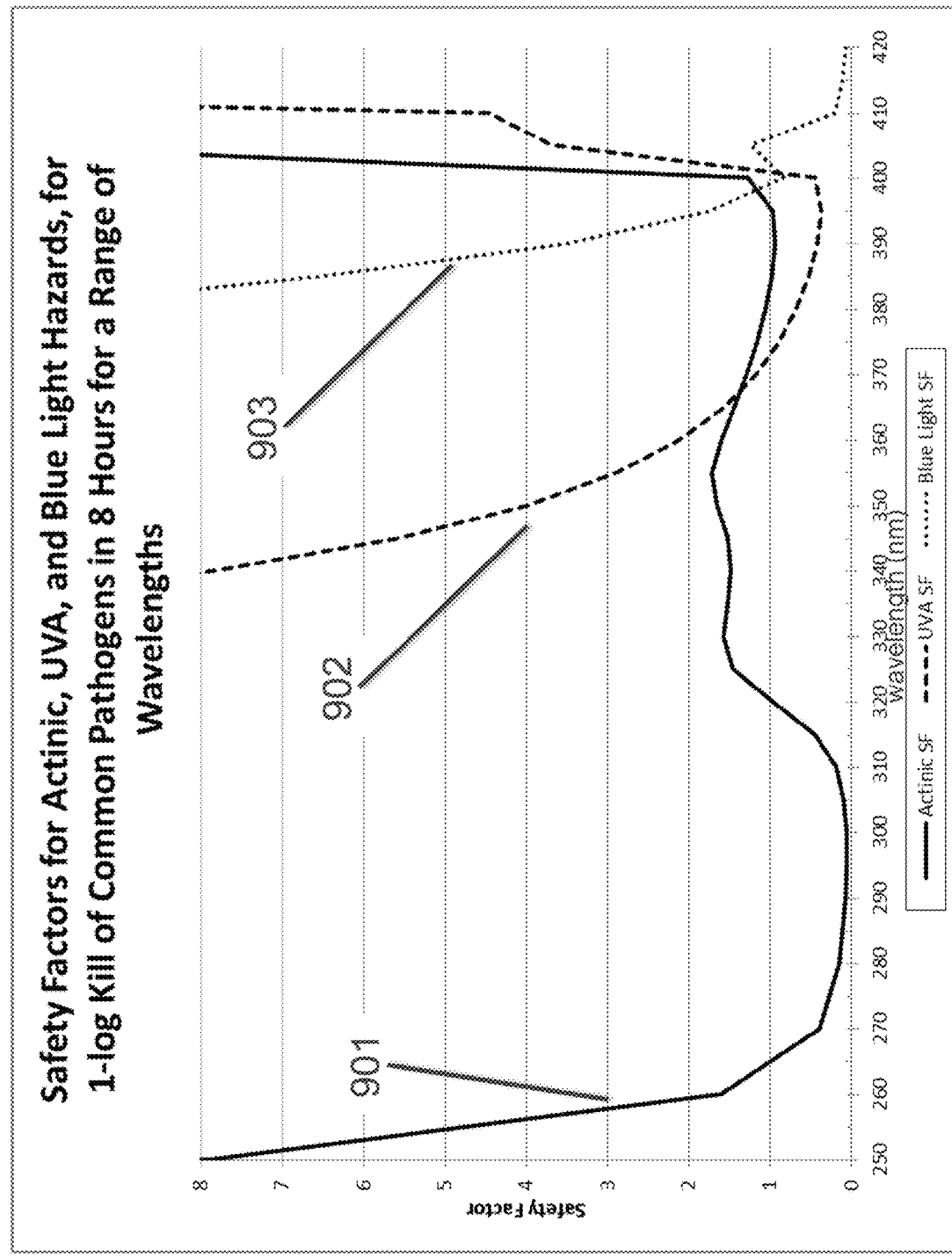
FIG. 9*a* illustrates the safety factors of exposure of humans to light needed for disinfection at various wavelengths for three hazard functions.
Figure 9B:
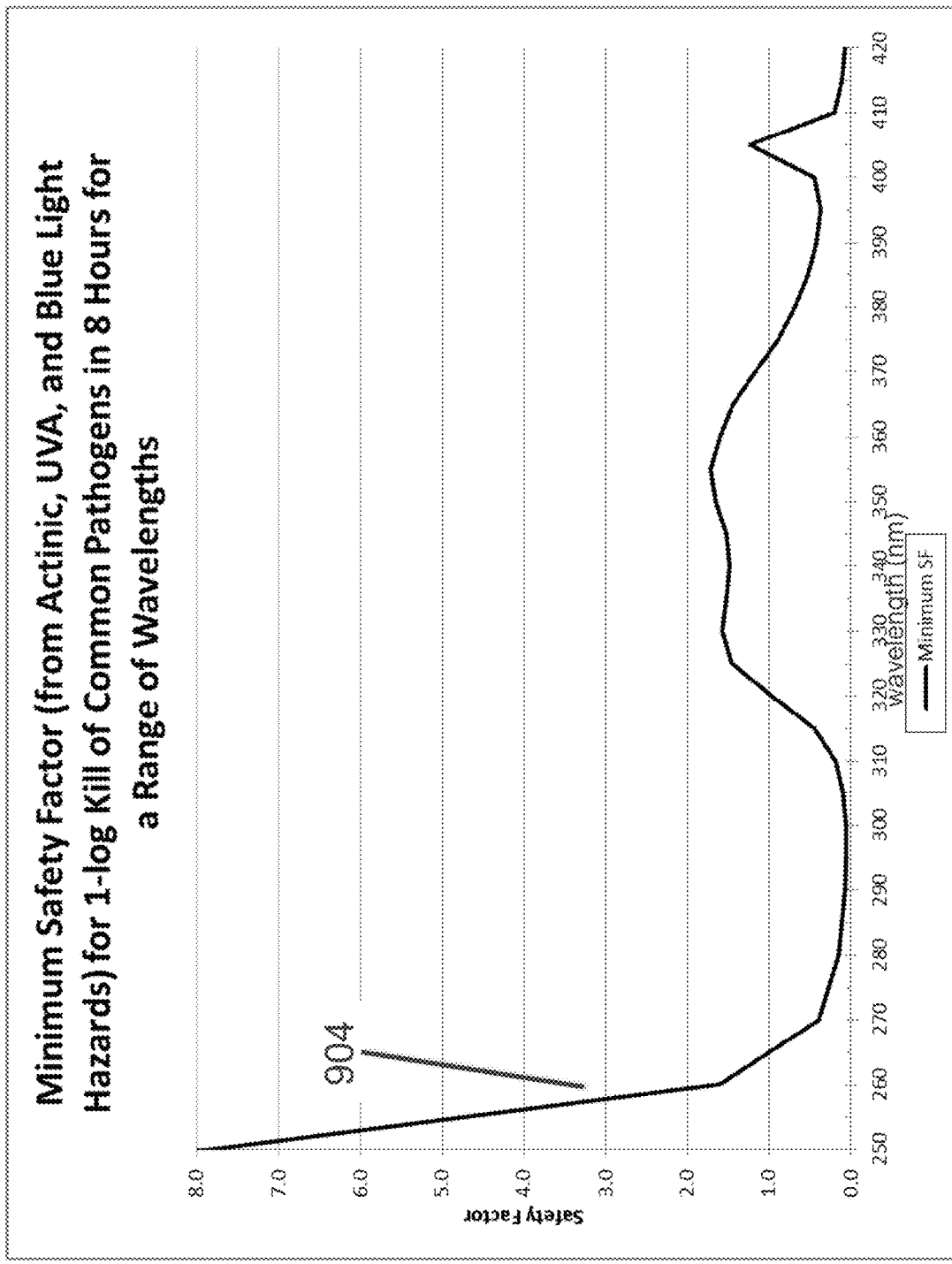
FIG. 9b illustrates the minimum safety factor of exposure of humans to light needed for disinfection at various wavelengths.
Figure 9C:
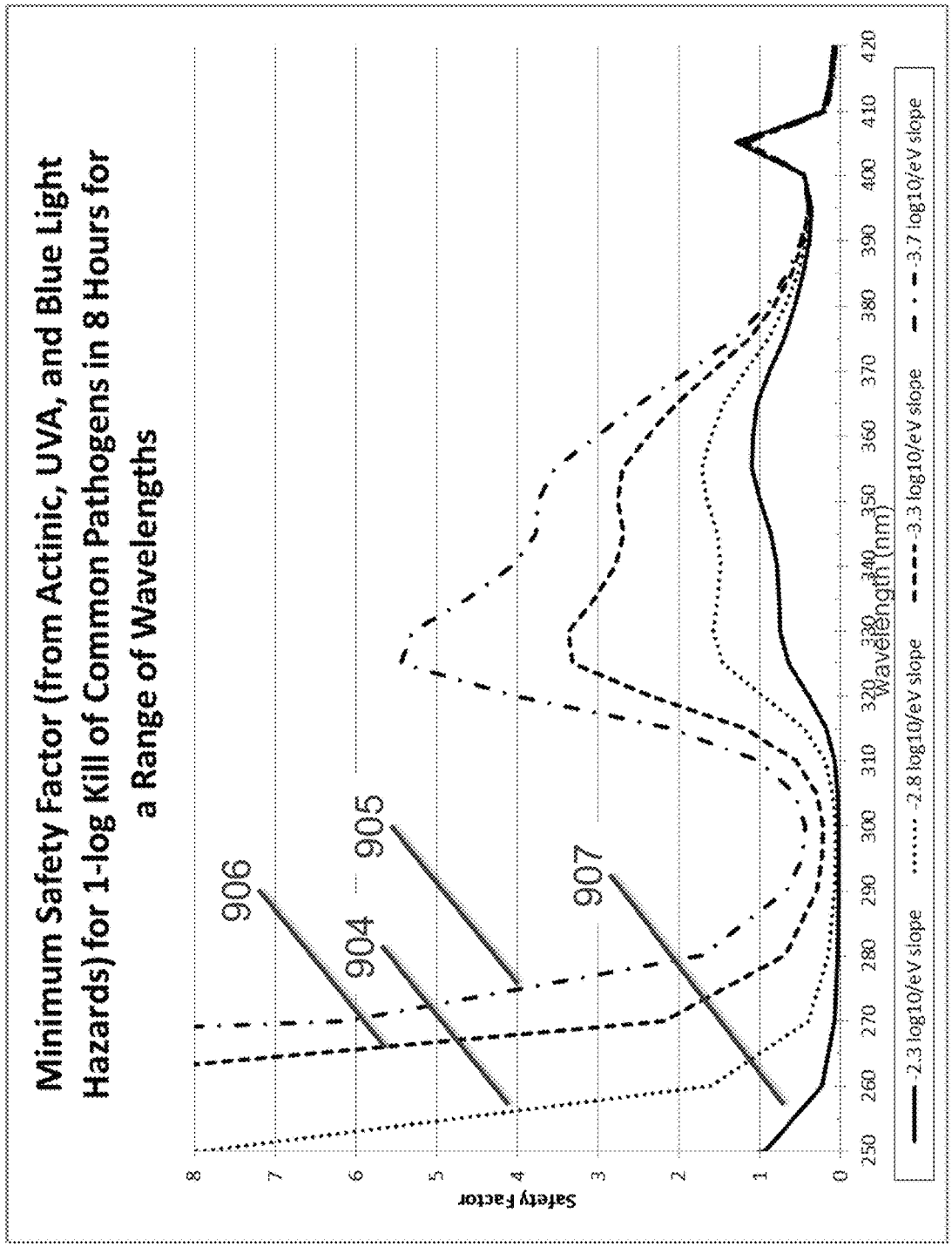
FIG. 9c illustrates the minimum safety factor of exposure of humans to light disinfection at various wavelengths for a range of trend line fits.

The safety factor for the Actinic UV, UVA, and Blue Light Hazard are shown for a range of wavelengths in FIGS. 9a-9c. Line 901 in FIG. 9a represents the safety factor for the Actinic UV hazard function over a range of 250-420 nm. Values of 1 or greater represent that a light disinfection system would be able to inactivate 90% of pathogens in 8 hours while being safe for a human. The effectiveness of the inactivating portion of the light at a given wavelength is determined by Equation 1 with the slope −1/z(E)=−2.8 $\log_{10}$ per eV. Line 902 and 903 represent the safety factors for UVA and Blue Light hazards, respectively. Line 904 in FIG. 9b represents the minimum safety factor at each wavelength (the minimum of the Actinic, UVA, and Blue Light safety factors represented by lines 901, 902, and 903 in FIG. 9a). This shows that the 405 nm inactivating light of the prior art is safe for this pathogen inactivation rate, but that 400 nm and 410 nm inactivating is not safe. Because commercially produced LEDs have some variance in their peak wavelength emission, the use of 405 nm LEDs must be tightly controlled in practice, so as to avoid using LEDs at slightly longer or shorter wavelengths that may be hazardous to humans. Line 904 also shows that the present invention allows the safe use of inactivating light in the range of 320-370 nm at this pathogen kill rate. This wide range of acceptable wavelengths allows for the use of commercially produced and binned LEDs without requiring that the peak wavelength of their emission be tightly controlled. Lines 905, 906, and 907 in FIG. 9c show additional curves for minimum safety factor for different values of −1/z(E) (−3.7, −3.3, and −2.3 $\log_{10}$/eV, respectively), along with Line 904 from FIG. 9b which represents −1/z(E)=−2.8 $\log_{10}$/eV. Line 905 shows a local maximum safety factor of 5.4 at 325 nm, with a safe range of 310-380 nm. Line 906 shows a local maximum safety factor of 3.4 at 330 nm, with a safe range of 315-375 nm. Line 904 shows a local maximum safety factor of 1.7 at 355 nm, with a safe range of 320-370 nm. Line 907 shows a local maximum safety factor of 1.1 at 355 nm, with a safe range of 350-365 nm. Additionally, lines 905, 906, and 904 show a safe area at low wavelengths (less than about 280, 270, or 260 nm respectively). This indicates that due to the increased pathogen inactivation ability shown by the kinetic model, these UV-C wavelengths may be able to achieve 90% pathogen inactivation over 8 hours of exposure while being safe for humans.

Also indicated in Tables 3b and 3c are the shifts in color point (Du'v') in the International Commission on Illumination (CIE) 1976 (u'v') chromaticity diagram. The maximum allowable color shift or color difference that is specified by customers in many typical LED lighting systems is Du'v'<0.007 or <0.005, and sometimes <0.002. The Du'v' values indicated in Tables 3b and 3c pertain to the flux of disinfection lighting required to inactivate 90% or 99% of *S. aureus*, respectively, added to and mixed with a flux of typical white lighting (e.g. 4000 K, 80 CRI, on the blackbody locus) at an illuminance of 500 lux (lumens/m$^2$), which is a typical indoor illuminance. Values of Du'v' exceeding about 0.007 or about 0.005 or about 0.002 indicate that the illumination provided by the mixture of the white light with the disinfecting light are shifted too far away from the target color point of the white light to be acceptable in most customer applications, requiring a correction to the color point by addition of a third component of light to offset the color shift created by the disinfection component of the light. Tables 3b and 3c indicate that Du'v' does not exceed 0.006 for either 365 nm or 325 nm disinfection lighting, at either 90% or 99% disinfection levels, but that 405 nm disinfection lighting exceeds even the most relaxed limit of Du'v'<0.007 by more than 40×, so that the color appearance of the mixed light is so far away from the color point specification, that an extreme amount of color correction is required from the third component of the light which significantly increases the complexity, the color stability, and potentially the cost of the lighting system.

The extreme color distortion that is indicated by Du'v' values of 0.236 or 0.317 when using 405 nm light to achieve 90% or 99% inactivation of *S. aureus* are indicative of the extremely unusual appearance of the mixture of disinfection light with standard white light, when uncorrected by the third component of light. However, even though the third component of light may mask the distortion of the white light caused by the extreme amount of 405 nm disinfection light, and even though it may correct the color point of the overall lighting system, it does not reduce the extremely high flux of 405 nm light, which is still received, unabated, by the retina of the human subject. Such extremely high levels of blue or violet or near UV light are well known to cause physiological disturbances including headache, dizziness, nausea, and others. Those adverse side effects of the disinfection component of the lighting have not appeared in our testing of subjects using 365 nm light at doses high enough to provide 90% or 99% inactivation of *S. aureus*. The reasons why 365 nm and other UV wavelengths may avoid the adverse physiological reactions of human subjects is because those wavelengths are nearly imperceptible to the human eye, and because the flux of disinfection light required for 90-99% inactivation of pathogens is much lower below about 380 nm than in the visible wavelength ranges, including the 380-400 nm range, and longer wavelength ranges.

Figure 6:
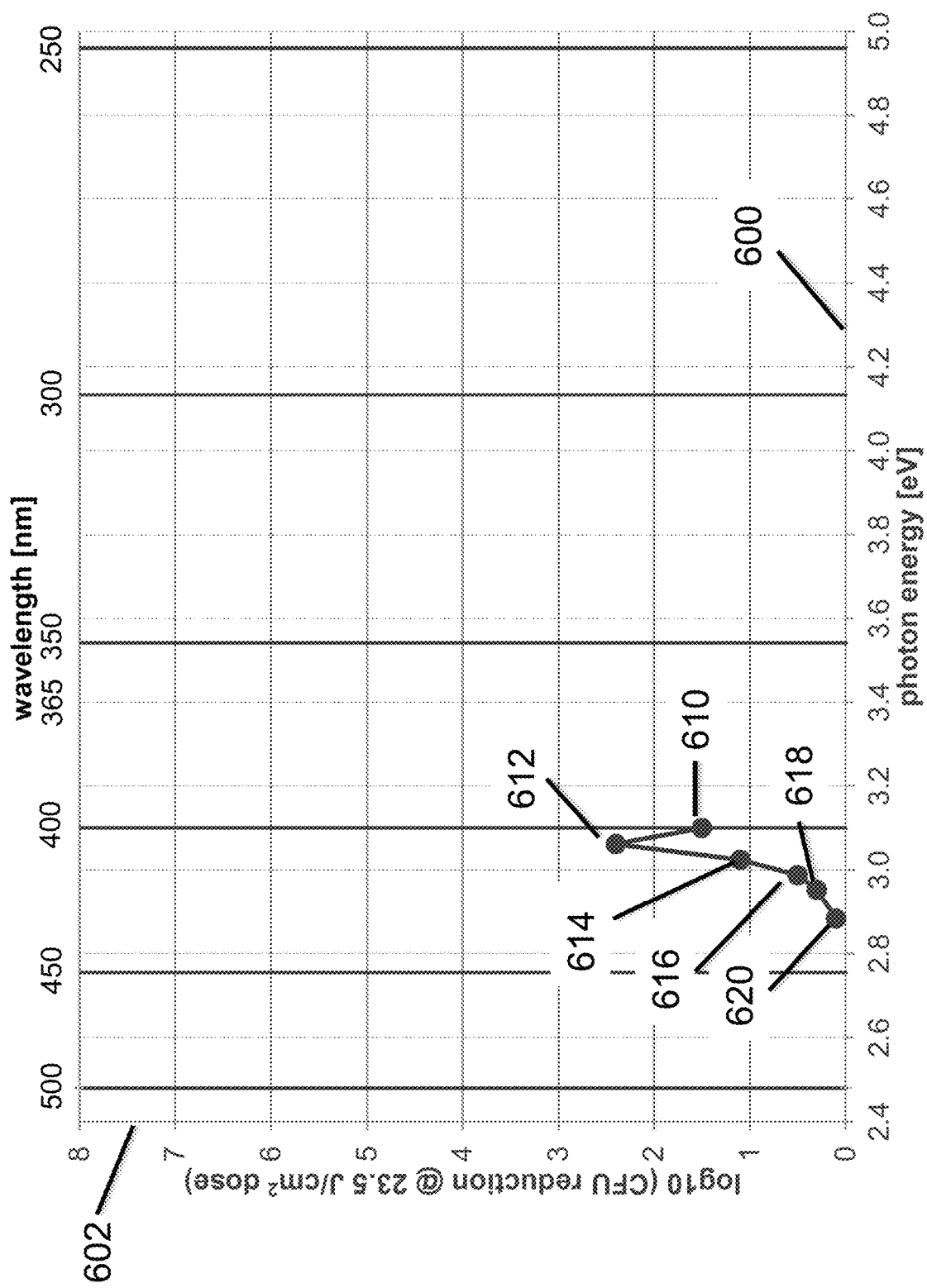
FIG. 6 illustrates a dataset of the reduction of *S. aureus* for a given dose of 23.5 J/cm$^2$ as a function of wavelength according to one example.

The inactivation rates 610, 612, 614, 616, 618, 620 in FIG. 6 represent the rates at which the pathogen *Staphylococcus aureus* was inactivated by exposure of narrow-band light having peak emission wavelengths at 400, 405, 410, 415, 420, 425 nm, respectively, as described in the Maclean 2008 reference. The inactivation rate vs. wavelength is shown to have a peak 612 at 405 nm, which is a typical preferred peak emission wavelength in some known systems. It is proposed in the U.S. Pat. Nos. 8,398,264 and 9,039,966 that the peak at about 405 nm is due to resonant absorption of the photon by a porphyrin molecule resident on the surface of the pathogen, resulting in generation of reactive oxygen species leading to inactivation of the pathogen. Herein, this resonance absorption can be referred to as the Porphyrin Hypothesis. The Porphyrin Hypothesis states that the ideal wavelength range for inactivation of pathogens without exceeding photobiological hazard limits may be between 380 nm and 420 nm, and especially at or near 405 nm. The data and calculations provided herein demonstrate that a different hypothesis, the First-order Kinetic Hypothesis, has guided discovery of greatly enhanced inactivation rates at wavelengths below about 380 nm, which unexpectedly resolve the major shortcomings of the prior art, including providing higher electrical system efficiency; lower system cost; less distortion of the color point when mixed with white light; reduced or eliminated physiological disturbance to humans; greater photobiological safety for humans; higher inactivation rate of pathogens. Although one or more embodiments of the system 100 described herein includes light source(s) 102 that generate light having wavelengths that extend into the hazard functions 310, 320, 330 the light is generated at a sufficiently low power that the risk to human beings exposed to the light is still sufficiently low to avoid harming the human beings. For example, the limit of exposure as specified by IEC 62471 to the blue light hazard function 330 is 100 watts per steradian per square meter. The light generated by the light source(s) 102 that falls within the blue light hazard function 300 may have a power density of no more than 100 watts per steradian per square meter, such as 100 watts or 5 watts per steradian per square meter or less.

As another example, the limit of exposure as specified by IEC 62471 to the UVA hazard function 320 may be 10 watts per square meter. The light generated by the light source(s) 102 that falls within the UVA hazard function 320 may have a power density of less than 10 watts per square meter, such as 4 watts or 0.5 watts per square meter or less. For example, the light source may generate the inactivating portion of the light such that the light includes no more than 10 watts or no more than 4 watts 0.5 watts of ultraviolet A light (e.g., the wavelengths of light falling within the range of the UVA hazard function 302) per square meter of floor area in the environment 104.

As another example, the limit of exposure as specified by IEC 62471 to the actinic hazard function 310 may be 0.001 watts per square meter. The light generated by the light source(s) 102 that falls within the actinic hazard function 310 may have a power density of less than 0.001 watts per square meter, such as 0.0005 watts or 0.00015 watts per square meter or less. For example, the light source may generate the inactivating portion of the light such that the light includes no more than 0.001 watts or no more than 0.0005 watts or no more than 0.00015 watts of actinic ultraviolet light (e.g., the wavelengths of light falling within the range of the actinic hazard function 304) per square meter of floor area in the environment 104.

Based on the preceding inactivation rates, power densities, and hazard functions, the lighting system 100 shown in FIG. 1 can generate light from the light sources 102 having an inactivating portion that inactivates pathogens on the surfaces or materials 106 in the environment 104 (e.g., without using a photosensitizer), where the inactivating portion of the light has a peak wavelength of no more than 380 nanometers and a flux density or power density of no more than 20 watts or 10 watts or 0.5 watts per square meter (e.g., of surface area or area on the floor of the environment 104) in order to ensure the safety of human beings exposed to the light. Such a light has been found to successfully inactivate a substantial amount of pathogens with a rapid inactivation rate.

In one example of the inventive subject matter described herein, irradiance tests were performed using a clinical wound-isolate of Staphylococcus aureus (ATCC #29213). Bacteria were inoculated and cultured overnight in tryptic soy broth (TSB) to high density at 37° C. with shaking. Before each experiment, overnight cultures were diluted back to log phase in fresh TSB and grown for approximately 2 hours at 37° C. with shaking. After 2 hours of re-culture, culture density was measured by optical density at 600 nm (OD600) and cell counts were estimated from a 0.5 McFarland standard (A600 of 0.132=1.5×10$^8$ CFU/mL, where CFU denotes Colony-Forming Units). Table 4 below outlines the cell density and serial dilution methodology for three test conditions.

TABLE 4

| Test condition | Initial Culture density (CFU/mL) | First Dilution | Second Dilution | Estimated Final Culture Density (CFU/mL) |
|---|---|---|---|---|
| A | 25.51 × 10$^8$ | 5 µL into 5 mL (TSB) | 178 µL into 19.8 mL (TSB) | ~2 × 10$^4$ |
| B | 31.25 × 10$^8$ | 5 µL into 5 mL (0.9% saline) | 128 µL into 19.8 mL (0.9% saline) | ~2 × 10$^4$ |
| C | 15.17 × 10$^8$ | 5 µL into 5 mL (TSB) | 264 µL into 19.7 mL (0.9% saline) | ~2 × 10$^4$ |

Approximately 5 mLs of diluted bacteria (Second Serial Dilution stock, ~2×10$^4$ CFU/mL) were transferred into Falcon Easy-Grip Tissue Culture polystyrene dishes (#353004, Corning Life Sciences). For all conditions, the lids of the Petri dishes were removed during light irradiation. Petri dishes were placed inside a steel housing to block ambient outside light. LED lamps were mounted onto the steel housings to irradiate the Petri dish test samples from a separation distance of 4 inches. All irradiation experiments were conducted inside a Biosafety Cabinet with a stainless steel working surface. Control samples were incubated in the dark under a lamp head with no connected power.

Petri dish test-samples were exposed to LED light having peak wavelengths of 404 nm or 369 nm for 4 hours and bacteria were plated onto solid TSB agar for standard Colony-Forming Unit (CFU) analysis. The culture was mixed and diluted into either sterile TSB or 0.9% saline by 10-fold serial dilution. Aliquots of 100 µL were pipetted onto solid TSB agar plates (in duplicate) and spread using glass beads. Plates were incubated for 12-24 hours at 37° C. and resulting colonies were enumerated. Viable cell density (per mL) was calculated by multiplying the number of colonies (per plate) by a 10-fold plating dilution and any appropriate serial-dilution factors thereafter. Table 5 below summarizes the growth results of these experiments at 404 nm and 369 nm for each of the tested conditions described above. In some cases, bacterial growth on the plate was too numerous to count (TNTC). The results from control samples generally agreed with the estimated inoculum of approximately 2×10$^4$ CFU/mL.

TABLE 5

| Test Condition | Light Exposure | Non-diluted colony count | 10-fold diluted colony count | 100-fold diluted colony count | Average CFU/mL |
|---|---|---|---|---|---|
| A | Control | TNTC | TNTC | Plate 1: 38 Plate 2: 69 | 5.35 × 10$^4$ |
| A | 369 nm | Plate 1: 0 Plate 2: 0 | Plate 1: 0 Plate 2: 0 | Plate 1: 0 Plate 2: 0 | 0 |
| A | 404 nm | Plate 1: 0 Plate 2: 0 | Plate 1: 0 Plate 2: 0 | Plate 1: 0 Plate 2: 0 | 0 |
| B | Control | TNTC | Plate 1: 150 Plate 2: 100 | NA | 1.25 × 10$^4$ |
| B | 369 nm | Plate 1: 0 Plate 2: 0 | Plate 1: 0 Plate 2: 0 | NA | 0 |
| B | 404 nm | TNTC | Plate 1: 79 Plate 2: 50 | NA | 6.45 × 10$^3$ |
| C | Control | TNTC | Plate 1: 150 Plate 2: 125 | Plate 1: 11 Plate 2: 18 | 1.41 × 10$^4$ ± 3.07 × 10$^3$ |
| C | 369 nm | Plate 1: 6 Plate 2: 5 | Plate 1: 0 Plate 2: 2 | Plate 1: 0 Plate 2: 0 | 7.75 × 10$^1$ ± 8.58 × 10$^1$ |
| C | 404 nm | Plate 1: 130 Plate 2: 125 | Plate 1: 11 Plate 2: 20 | Plate 1: 1 Plate 2: 1 | 1.28 × 10$^3$ ± 3.76 × 10$^2$ |

The results of these experiments demonstrate several novel findings. First, by comparing conditions A-C, it is revealed that the antibacterial activity of 404 nm light is potentiated by media components in rich media (i.e., condition A versus condition B), even when trace amounts of TSB media are carried over by dilution (i.e., condition C versus condition B). This finding is consistent with the understanding that photo-inactivation at 404 nm was found to be dependent on light-sensitive components in rich media, as described in Tomb et al., *Inactivation of Streptomyces phage ɸC31 by 405 nm light*, Bacteriophage 4, e32129; January-December 2014.

In contrast, the antibacterial activity of 369 nm light (e.g., the inactivating portion of the light generated by one or more of the light sources 102 shown in FIG. 1 according to one embodiment) is generally unbiased by media test conditions and inactivates bacteria to a greater degree under all test conditions (A-C). Interestingly, by comparing conditions A-C, it is suggested that light-sensitive components in rich media might exert inverse effects at 369 nm light compared to 405 nm light, depending on the concentration of media components.

Figure 4:
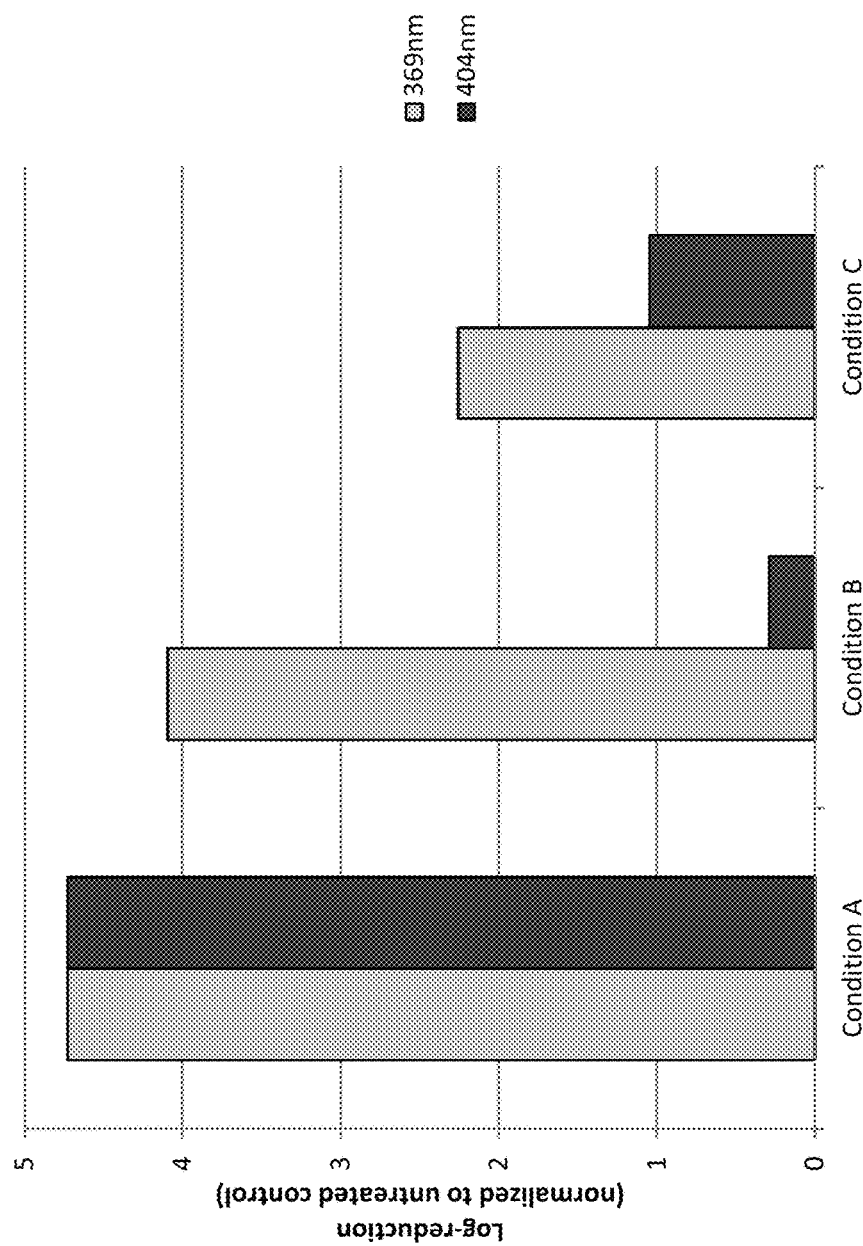
FIG. 4 illustrates a bar graph of log-reduction at a wavelength of light of 369 nm compared to a wavelength of 404 nm for several tested conditions according to one example.

FIG. 4 illustrates a bar graph of log-reduction at 369 nm compared to 404 nm for the tested conditions A-C (normalized to untreated controls). This data generally illustrates that 369 nm light photo-inactivates bacteria via different environmental and mechanistic parameters than 404 nm light.

In another example, irradiance tests were performed using a clinical wound-isolate of Staphylococcus aureus (ATCC #29213). Bacteria were inoculated and cultured overnight in tryptic soy broth (TSB) to high density at 37° C. with shaking. Before each experiment, overnight cultures were diluted back to log phase in fresh TSB and grown for approximately 2 hours at 37° C. with shaking. After 2 hours of re-culture, culture density was measured by optical density at 600 nm (OD600) and cell counts were estimated relative to a 0.5 McFarland standard (A600 of 0.132≅1.5× 10$^8$ CFU/mL). Bacteria were diluted to ~2×10$^4$ CFU/mL in isotonic saline as described in Table 4 for Condition B in order to avoid artifacts associated with irradiance of rich media (as described above in connection with the preceding example).

Approximately 5 mLs of diluted bacteria were transferred into Falcon Easy-Grip Tissue Culture polystyrene dishes (#353004, Corning Life Sciences), and the lids of the Petri dishes were removed during light irradiation. Petri dishes were placed inside a steel housing to block ambient outside light and LED lamps were mounted on the steel housings to irradiate bacteria from a separation distance of 4 inches. All irradiation experiments were conducted inside a Biosafety Cabinet with a stainless steel working surface. Control samples were incubated in the dark under a lamp head with no connected power.

Petri dish test-samples were exposed to LED light having peak wavelengths of 404 nm, 388 nm, or 369 nm for 2-4 hours, and bacteria were plated onto solid TSB agar for standard Colony-Forming Unit (CFU) analysis. The culture was mixed and diluted into either sterile TSB or 0.9% saline by 10-fold serial dilution, and aliquots of 100 µL were pipetted onto solid TSB agar plates (in duplicate) and spread using glass beads. Plates were incubated for 12-24 hours at 37° C. and resulting colonies were enumerated. Viable cell density (per mL) was calculated by multiplying the number of colonies (per plate) by a 10-fold plating dilution and any appropriate serial-dilution factors thereafter. Table 6 below summarizes the results of these experiments for the irradiance conditions described above. In some cases, bacterial growth on the plate was too numerous to count (TNTC). The results from control samples generally agreed with the estimated inoculum of approximately $2 \times 10^4$ CFU/mL.

TABLE 6

| Exposure Time | Light Exposure | Non-diluted colony count | 10-fold diluted colony count | 100-fold diluted colony count | Average CFU/mL |
|---|---|---|---|---|---|
| 2 hrs | Control | TNTC | Plate 1: 183 Plate 2: 139 | Plate 1: 14 Plate 2: 15 | $1.53 \times 10^4 \pm 2.06 \times 10^3$ |
| 2 hrs | 369 nm | TNTC | Plate 1: 71 Plate 2: 72 | Plate 1: 5 Plate 2: 4 | $5.83 \times 10^3 \pm 1.58 \times 10^3$ |
| 2 hrs | 388 nm | TNTC | Plate 1: 137 Plate 2: 122 | Plate 1: 9 Plate 2: NA | $1.16 \times 10^4 \pm 2.4 \times 10^3$ |
| 2 hrs | 404 nm | TNTC | Plate 1: 128 Plate 2: 96 | Plate 1: 10 Plate 2: 10 | $1.06 \times 10^4 \pm 1.48 \times 10^3$ |
| 3 hrs | Control | TNTC | Plate 1: 82 Plate 2: 90 | Plate 1: 9 Plate 2: NA | $8.73 \times 10^3 \pm 4.62 \times 10^2$ |
| 3 hrs | 369 nm | Plate 1: 0 Plate 2: 0 | Plate 1: 0 Plate 2: 0 | Plate 1: 0 Plate 2: 0 | 0 |
| 3 hrs | 388 nm | Plate 1: 34 Plate 2: 35 | Plate 1: 4 Plate 2: 3 | Plate 1: 0 Plate 2: 0 | $3.48 \times 10^2 \pm 4.11 \times 10^1$ |
| 3 hrs | 404 nm | TNTC | Plate 1: 90 Plate 2: 77 | Plate 1: 7 Plate 2: 9 | $8.18 \times 10^3 \pm 9.95 \times 10^2$ |
| 4 hrs | Control | TNTC | Plate 1: 100 Plate 2: 150 | NA | $1.25 \times 10^4$ |
| 4 hrs | 369 nm | Plate 1: 0 Plate 2: 0 | Plate 1: 0 Plate 2: 0 | NA | 0 |
| 4 hrs | 388 nm | Plate 1: 18 Plate 2: 28 | Plate 1: 3 Plate 2: 1 | NA | $2.15 \times 10^2$ |
| 4 hrs | 404 nm | TNTC | Plate 1: 79 Plate 2: 50 | NA | $6.45 \times 10^3$ |

Figure 5:
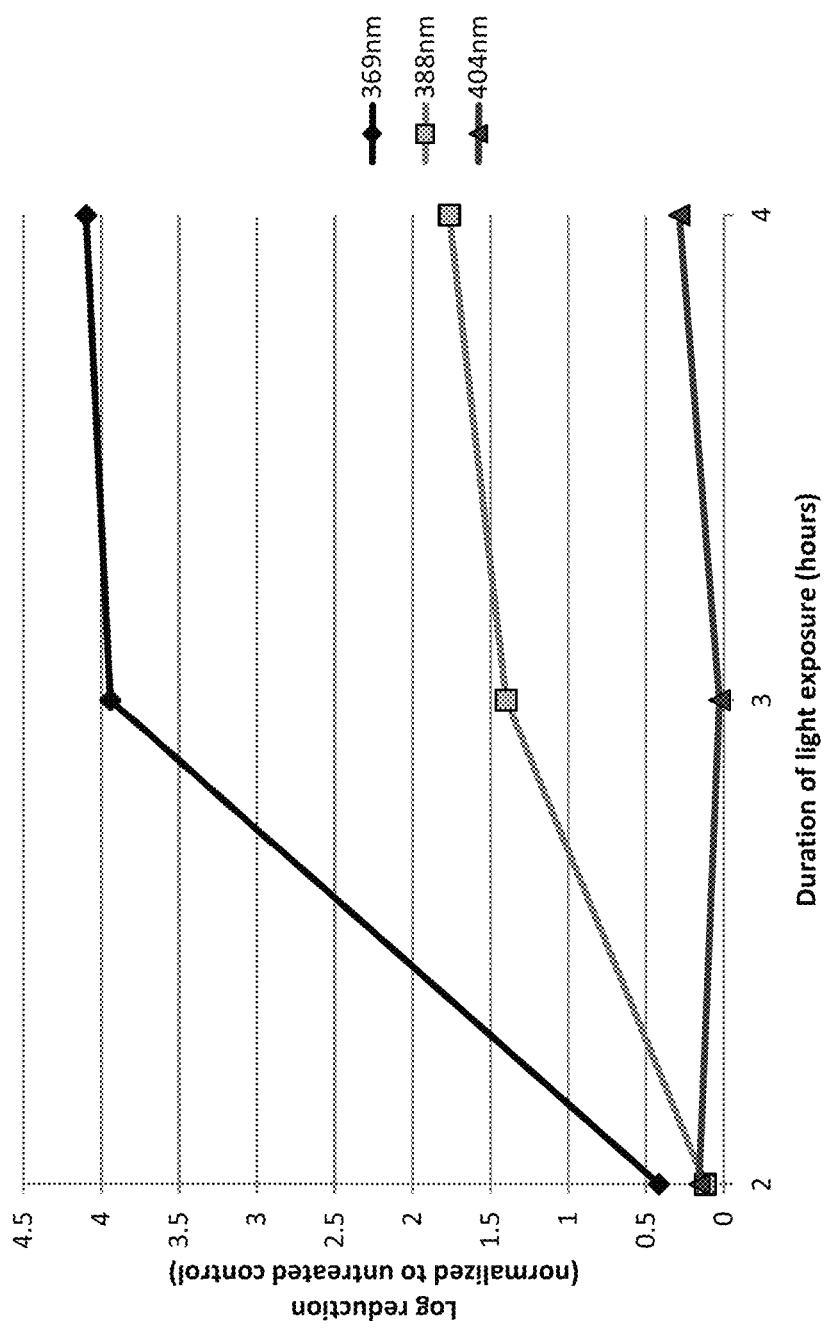
FIG. 5 depicts photo-inactivation kinetics of light having wavelengths of 369 nm, 388 nm, and 404 nm light after normalization to untreated controls according to one example.

The results of these experiments demonstrate several novel findings. First, by comparing the kinetics of photo-inactivation, it is revealed that 369 nm light rapidly inactivates at least 4-log of *Staphylococcus aureus* inoculant between 2-3 hours of exposure. Photo-inactivation using 388 nm light is approximately 2-fold less efficient than 369 nm light, and little to no photo-inactivation is observed with 404 nm light under these experimental parameters that minimize environmental artifacts from media components. FIG. 5 depicts the photo-inactivation kinetics of 369 nm, 388 nm, and 404 nm light after normalization to untreated controls.

The results achieved by these experiments demonstrate that the inactivation rate for inactivating pathogens unexpectedly and significantly increases as the wavelength of the inactivating portion of the light is decreased, while the power density of the inactivating portion of the light remains sufficiently low to be safe for human exposure to the light. Prior attempts to inactivate pathogens using light rely on light that either has short wavelengths and larger power densities, which poses significant risks of exposure to human beings due to the actinic health hazard 310 such that human beings cannot be present when a location is exposed to the light or the exposed location is not accessible to human beings. Other prior attempts rely on a light having a peak wavelength of 405 nm that predominantly lies between the UVA and blue light hazard functions 320, 330, but that also uses increased power densities and that is visible to human observers, which can cause undesirable effects to the exposed human observers, such as nausea, dizziness, etc. The reduced wavelength, reduced power light used by the lighting system 100 shown in FIG. 1 can produce light of shorter wavelengths and less power density, while being invisible to human observers, safe for exposure to human observers, and having an inactivation rate that is several orders of magnitude faster than the prior attempts.

A method for inactivating one or more pathogens by exposing the pathogens to light includes generating light from a light source that exposes one or more surfaces or materials to the light, where an inactivating portion of the light has a peak wavelength in the range of 300 to 380 nanometers in one embodiment.

In one embodiment, a lighting system includes a light source configured to generate light toward one or more surfaces or materials to inactivate one or more pathogens on the one or more surfaces or materials. The light includes an inactivating portion having wavelengths in a range of 280 to 380 nanometers.

In one example, the one or more pathogens that are inactivated by at least the inactivating portion of the light includes one or more of *staphylococcus, Clostridium difficile, streptococcus*, or bacterial pneumonia.

In one example, the light source is configured to generate the light toward the one or more surfaces or materials while also concurrently exposing one or more human beings to the light.

In one example, the light source is configured to generate the light toward the one or more surfaces or materials to inactivate the one or more pathogens without using a photosensitizer.

In one example, the light source is configured to generate the light so that the inactivating portion of the light is imperceptible to a human observer of the light.

In one example, the light source is configured to generate the inactivating portion of the light such that the inactivating portion of the light includes no more than 0.001 watts of actinic ultraviolet light per square meter of floor area.

In one example, the light source is configured to generate the inactivating portion of the light such that the inactivating portion of the light includes no more than 10 watts per square meter of floor area of ultraviolet A light.

In one example, the light source is configured to generate the inactivating portion of the light such that the inactivating portion of the light includes no more than 100 watts of blue light per steradian per square meter of floor area.

In one example, the light source is configured to generate the light such that a peak wavelength of the inactivating portion of the light is greater than 300 nanometers.

In one example, the light source is configured to generate the light such that the inactivating portion of the light includes wavelengths in a range of 320 to 380 nm.

In one example, the light source is configured to generate the light such that the inactivating portion of the light has a peak wavelength in a range of 320 to 370 nm.

In one example, the light source is configured to generate the light such that the inactivating portion of the light is pulsed, for example, at a frequency exceeding 100 hertz with a duty factor of less than 0.5.

In one example, the light source is configured to generate the light such that the inactivating portion of the light is pulsed, for example, at a frequency exceeding 100 hertz with a duty factor of less than 0.1.

In one example, the light source generates the light to include the inactivating portion of the light with wavelengths in a range of 280 to 380 nanometers, and a second portion of the light having longer wavelengths.

In one embodiment, a method for inactivating one or more pathogens and optionally concurrently illuminating a room having one or more human occupants in to while the pathogens are inactivated is provided. The method includes generating light from a light source toward one or more surfaces or materials to inactivate the one or more pathogens on the one or more surfaces or materials. The light is generated with an inactivating portion of the light including wavelengths in a range of 280 to 380 nanometers.

In one example, the one or more pathogens that are inactivated by at least the inactivating portion of the light includes one or more of *staphylococcus, Clostridium difficile, streptococcus*, or bacterial pneumonia.

In one example, the light source is configured to generate the light toward the one or more surfaces or materials while also concurrently exposing one or more human beings to the light.

In one embodiment, a lighting system includes a light source configured to generate light toward one or more surfaces or materials to inactivate one or more pathogens on the one or more surfaces or materials. The light source is configured to generate the light at a power density of no more than five watts per square meter at an exposed area of the one or more surfaces or materials with an inactivating portion of the light including wavelengths in a range of 280 to 380 nanometers, including no more than 0.001 watts of actinic ultraviolet light per square meter of floor area, including no more than 10 watts per square meter of floor area of ultraviolet A light, and including no more than 100 watts of blue light per steradian per square meter of floor area.

In one example, the one or more pathogens that are inactivated by at least the inactivating portion of the light includes one or more of *staphylococcus, Clostridium difficile, streptococcus*, or bacterial pneumonia.

In one example, the light source is configured to generate the light toward the one or more surfaces or materials while also concurrently exposing one or more human beings to the light.

In one example, the light source is configured to generate the light so that the inactivating portion of the light is imperceptible to a human observer of the light.

The foregoing description of certain embodiments of the inventive subject matter will be better understood when read in conjunction with the appended drawings. The various embodiments are not limited to the arrangements and instrumentality shown in the drawings. The above description is illustrative and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Other embodiments may be apparent to one of ordinary skill in the art upon reviewing the above description. The scope of the inventive subject matter should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure. And, as used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A disinfection system comprising:
   a disinfection light source configured to emit UVC light into an environment for human occupancy, the UVC light having its peak wavelength below 280 nanometers;
   wherein the disinfection light source is configured to produce an actinic dose at a target surface in the environment of 30 J/m² or less over a 10,000 second period.

2. The disinfection system of claim 1 wherein the UVC light has its peak wavelength below 270 nanometers.

3. The disinfection system of claim 1 wherein the UVC light has its peak wavelength below 260 nanometers.

4. The disinfection system of claim 1 wherein the UVC light has its peak wavelength at 240 nanometers or higher.

5. The disinfection system of claim 1 wherein the disinfection light source is configured to produce an actinic dose at a target surface in the environment of 30 J/m² or less over a 30,000 second period.

6. The disinfection system of claim 1 wherein the environment for human occupancy is a hospital room, a doctor's office, a dentist office, a school or room in a school, bathroom, or a public area.

7. The disinfection system of claim 1 further comprising:
a room, wherein the environment for human occupancy is the room and the disinfection light source is arranged to emit the UVC light into the room.

8. The disinfection system of claim 1 wherein the disinfection light source comprises LEDs.

9. The disinfection system of claim 1 further comprising:
a white light source arranged to illuminate the environment for human occupancy.

10. The disinfection system of claim 9 wherein the disinfection light source is configured to continuously operate to emit the UVC light into the environment for human occupancy independently of the illumination provided by the white light source.

11. The disinfection system of claim 1 further comprising:
a controller operative to control the disinfection light source to pulse the UVC light.

12. A disinfection method comprising:
inactivating one or more pathogens in an environment for human occupancy by emitting UVC light having its peak wavelength below 280 nanometers into the environment for human occupancy;
wherein the UVC light is emitted with actinic UV irradiance below 0.003 W/m² at a target surface in the environment.

13. The disinfection method of claim 12 wherein the UVC light has its peak wavelength below 270 nanometers.

14. The disinfection method of claim 12 wherein the UVC light has its peak wavelength below 260 nanometers.

15. The disinfection method of claim 12 wherein the UVC light has its peak wavelength at 240 nanometers or higher.

16. The disinfection method of claim 12 wherein the UVC light is emitted with actinic UV irradiance below 0.001 W/m².

17. The disinfection method of claim 12 further comprising:
illuminating the environment for human occupancy with white light.

18. The disinfection method of claim 17 wherein:
the UVC light is continuously emitted into the environment for human occupancy independently of the illuminating of the environment for human occupancy with white light.

19. The disinfection method of claim 12 wherein the emitting of the UVC light includes pulsing the UVC light.

20. The disinfection method of claim 12 wherein the emitting of the UVC light into the environment for human occupancy is effective to inactivate at least 90% of the one or more pathogens over eight hours of exposure.

* * * * *